United States Patent [19]

Oi et al.

[11] 4,298,605
[45] Nov. 3, 1981

[54] CEPHALOSPORIN DERIVATIVES

[75] Inventors: Nobuhiro Ōi, Hoya; Bunya Aoki, Tama; Teizo Shinozaki, Matsudo; Kanji Moro, Kuki; Isao Matsunaga; Takao Noto, both of Tokyo; Toshiyuki Nebashi, Kawagoe; Yusuke Harada, Tokyo; Hisao Endo, Yokohama; Takao Kimura, Chiba; Hiroshi Okazaki, Sayama; Haruki Ogawa, Chofu; Minoru Shindo, Tokyo, all of Japan

[73] Assignee: Chugai Seiyaku Kabushiki Kaisha, Tokyo, Japan

[21] Appl. No.: 47,781

[22] Filed: Jun. 11, 1979

[30] Foreign Application Priority Data

Jun. 22, 1978 [JP] Japan .................................. 53-74868
Sep. 11, 1978 [JP] Japan .................................. 53-110627
Apr. 26, 1979 [JP] Japan .................................. 54-50841

[51] Int. Cl.$^3$ .......................................... C07D 501/36
[52] U.S. Cl. ..................................... 424/246; 544/26; 544/21; 544/30
[58] Field of Search ............................ 544/26, 27, 21; 424/246

[56] References Cited

U.S. PATENT DOCUMENTS

| 3,687,949 | 8/1972 | Holdreye | 260/243 C |
| 3,925,368 | 12/1975 | Cooper et al. | 260/240 J |
| 4,061,630 | 12/1977 | Herron | 544/15 |
| 4,080,451 | 3/1978 | Baxter et al. | 544/26 |
| 4,100,346 | 7/1978 | Gottstein et al. | 544/27 |
| 4,143,166 | 3/1979 | Takaya et al. | 544/26 |
| 4,144,391 | 3/1979 | Hatfield | 544/21 |

FOREIGN PATENT DOCUMENTS

| 2653621 | 6/1977 | Fed. Rep. of Germany . |
| 2731935 | 1/1978 | Fed. Rep. of Germany . |
| 52-5787 | 1/1977 | Japan . |
| 1518722 | 4/1977 | United Kingdom . |
| 1479711 | 7/1977 | United Kingdom . |
| 1498025 | 1/1978 | United Kingdom . |
| 1505885 | 3/1978 | United Kingdom . |
| 1508314 | 4/1978 | United Kingdom . |
| 1521073 | 8/1978 | United Kingdom . |
| 1525626 | 9/1978 | United Kingdom . |

Primary Examiner—Nicholas S. Rizzo
Attorney, Agent, or Firm—Browdy and Neimark

[57] ABSTRACT

Cephalosporin derivatives which have an excellent antibacterial action particularly against bacteria belonging to genus Pseudomonas or Serratia and are represented by the formula:

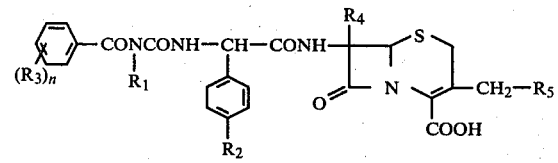

wherein $R_1$, $R_2$, $R_3$, $R_4$, $R_5$ and n are as defined in the specification, and salts thereof; a process for preparing the same; and an antibacterial preparation containing the same as an active ingredient are disclosed.

9 Claims, No Drawings

CEPHALOSPORIN DERIVATIVES

This invention relates to a cephalosporin derivative which has a broad antibacterial spectrum and exhibits antibacterial activity against various gram-negative and positive bacteria.

More particularly, this invention relates to a cephalosporin derivative represented by the following formula and its salt,

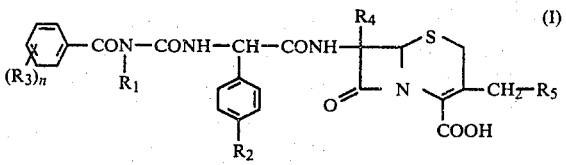

wherein $R_1$ is a hydrogen atom or a lower alkyl group; $R_2$ is a hydrogen atom or a hydroxyl group; $R_3$ is a hydroxyl group or a lower alkanoyloxyl group; n is 2 or 3; at least two of $R_3$ are bonded to adjacent carbon atoms, the position of substituent $R_3$ being selected from 3 to 5 position when $R_1$ is a lower alkyl group and $R_3$ is a hydroxyl group, and 2 to 6 position when $R_1$ and $R_3$ are other substituents; $R_4$ is a hydrogen atom or a methoxyl group; and $R_5$ is an acetoxyl group or —S—$R_6$ (wherein $R_6$ is a five-membered heterocyclic ring including one or more nitrogen atoms and optionally a sulfur atom, which is unsubstituted or substituted with a lower alkyl group).

Cephalosporin derivatives having a benzoylureido group bonded at α-position of 7-acylamido side chain of the derivatives have been reported, for example, in U.S. Pat. Nos. 3,925,368 and 4,061,630, British Pat. Nos. 1,479,711; 1,498,025; 1,505,885; 1,508,314; 1,518,722 and 1,521,073 and West German Offenlegungsschrift No. 2,653,621. However, none of such references refers to a hydroxyl group or a lower alkanoyloxyl group as a substituent of the corresponding benzoyl group.

Although U.S. Pat. No. 3,687,949, British Pat. No. 1,525,626 and Japanese Patent Disclosure No. 5787/77 refer to a lower alkanoyloxyl group as the substituent, they do not refer to a hydroxyl group. However, the above three references disclose only in the general description the lower alkanoyloxyl group as one of the several substituents and have no disclosure that suggests two or three lower alkanoyloxy groups and bonding at least two of the groups to adjacent carbons. Furthermore, no specific compound having lower alkanoyloxyl group(s) as the substituent of the benzoyl group is disclosed in the references.

As explained hereinabove, the cephalosporin derivative of this invention represented by the formula (I) is novel.

The derivative of this invention exhibits high antibacterial activity against both gram-positive and negative bacteria. Especially against bacteria belonging to Pseudomonas or Serratia, the compound of this invention exhibits remarkably higher antibacterial activity than cefazorin, cephaloridine or other widely used cephalosporin antibiotics.

The object compound of this invention is excellent in behavior in vivo after administration, such as absorption, excretion, distribution, metabolism, etc. and also exhibits high ability to prevent infection from bacteria. Because of these properties, the compounds of this invention are useful as an antibacterial agent.

Among the compounds of this invention, a compound of the formula (I) wherein $R_3$ is a lower alkanoyloxyl group is not only useful itself but is also useful as an intermediate because the lower alkanoyl group is removed to give a compound of the formula (I) wherein $R_3$ is a hydroxyl group.

The lower alkyl group represented by $R_1$ of the formula (I) is a group having 1-4 carbon atoms which may or may not be branched, and include, for example, methyl, ethyl, n-propyl, isopropyl, n-butyl, isobutyl and t-butyl groups. Preferred examples are methyl and ethyl groups. The lower alkanoyl group of the lower alkanoyloxyl group represented by $R_3$ is a group having 2-4 carbon atoms which may or may not be branched, and includes, for example, acetyl, propionyl, n-butyryl and isobutyryl groups. The preferred example is an acetyl group.

When $R_1$ is a lower alkyl group and $R_3$ is a hydroxyl group, if the hydroxyl group is present on the benzoyl nucleus at 2- or 6-position, the ureido group becomes unstable thus restricting the position of substituent $R_3$. Therefore, when $R_1$ is a lower alkyl group and $R_3$ is a hydroxyl group, the position of substituent $R_3$ is either 3- and 4-position or 3-, 4- and 5-position. For other combinations of $R_1$ and $R_3$, the position of substituent $R_3$ is either 2- and 3-position, 3- and 4-position, 2-, 3- and 4-position, 3-, 4- and 5-position, 2-, 4- and 5-position, 2-, 3- and 5-position or 2-, 3- and 6-position; 2- and 3-position, 3- and 4-position or 3-, 4- and 5-position is preferred.

The heterocyclic group having five members which is represented by $R_6$ of the formula (I) includes, for example, 1,3,4-thiadiazole, triazole, and tetrazole, which may or may not be substituted with one or more lower alkyl groups. The lower alkyl is a group having 1-3 carbon atoms, which may or may not be branched, and includes, for example, methyl, ethyl, n-propyl and isopropyl groups. A methyl group is preferred.

Since the cephalosporin derivative of this invention has a carboxyl group, it is capable of forming salts with various basic substances with the group. All these salts are also covered by the scope of this invention. Examples of a salt of the compound according to this invention are inorganic basic salts, for example, salts of alkali metals such as sodium and potassium, salts of alkaline earth metal such as calcium, and organic basic salts, for example, procain and dibenzylethylenediamine salts. These salts can be prepared by a conventional way, that is, by treating a free carboxyl group of the cephalosporin derivative with the above described inorganic or organic bases.

Due to the asymmetric carbon atom in 7-acetamido group, some end compounds of this invention have their optical isomers, i.e. DL-, D- and L-isomers. All these isomers are also covered by the scope of this invention.

This invention also relates to a process for preparing a cephalosporin derivative of the formula (I) or its salt. According to one embodiment of this invention, the process comprises reacting 7-aminocephalosporin represented by the formula:

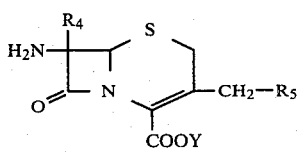

wherein $R_4$ and $R_5$ are as defined above and Y is a hydrogen atom or a protecting group for the carboxyl group, or its reactive derivative with a substituted ureidophenylacetic acid represented by the formula:

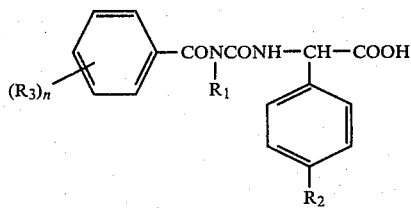

wherein $R_1$, $R_2$, $R_3$ and n are as defined above, or its reactive derivative and then, when Y is the protecting group, removing the group.

The reactive derivative of 7-aminocephalosporin of the formula (II) means a derivative, 7-amino group of which is activated into reactive form. For example, the introduction of a trimethylsilyl group into the 7-amino group can sufficiently cause the necessary amide-forming reaction.

When the compound of the formula (II) has a protecting group as Y, examples of the protecting group include groups capable of forming an ester with the carboxyl group, such a a trimethylsilyl or benzhydryl group. The trimethylsilyl group bonded with the carboxyl group is easily removed by treatment with water or alcohol, while the benzhydryl group is easily removed by the aid of trifluoroacetic acid.

Other examples of the protecting group for Y include organic or inorganic bases capable of forming a salt with the carboxyl group such as alkali metals, alkaline earth metals and tertiary amines such as triethylamine, N-methylpiperidine, N-methylmorpholine, pyridine and the like. The bases forming salts are removed by treatment with an acid.

The reactive derivatives of the substituted ureidophenylacetic acid of the formula (III) means a derivative of said acid, the carboxylic group of which is activated for reaction. Examples of said derivatives include acid anhydride, reactive ester or reactive amide. More particularly, they are a mixed acid anhydride with an aliphatic carboxylic acid such as pivalic acid, trichloroacetic acid or pentanoic acid; mixed anhydride with alkyl carbonate; mixed anhydride with phenylphosphoric acid; mixed anhydride with aromatic carboxylic acid; esters such as 1-hydroxybenzotriazolyl ester, 2,4-dinitrophenyl ester, N-hydroxysuccinimidyl ester, N-hydroxyphthalimidyl ester, pentachlorophenyl ester, phenylazophenyl ester, cyanomethyl ester and methoxymethyl ester; amides such as those with imidazole, triazole, tetrazole or the like. The reactive derivative of the substituted ureidophenylacetic acid of the formula (III) may be an acid halide if, in the formula (III), $R_3$ is a lower alkanoyloxyl group and $R_2$ is a hydrogen atom.

When a compound of the formula (II) wherein Y is a protecting group for the carboxyl group is used, the amide formation reaction may be carried out effectively by the use of a condensing agent such as a carbodiimide, for example, N,N'-dicyclohexylcarbodiimide, N,N'-diethylcarbodiimide, N-cyclohexyl-N'-morpholinoethylcarbodiimide, N,N'-diisopropylcarbodiimide or the like without previously converting the substituted ureidophenylacetic acid into its reactive derivative.

The amide-forming reaction is generally carried out in a solvent. The solvent which is useful in this reaction is an inert organic solvent such as acetone, tetrahydrofuran, dimethylformamide, pyridine, acetonitrile, dioxane, chloroform, dichloromethane or ethyl acetate. The solvents which are miscible with water may be used as aqueous mixture.

Although the reaction is generally carried out under cooling or at ambient temperature, it may be carried out under warming, depending on the particular reactants. However, the temperature usually ranges from $-30°$ to $35°$ C., preferably, from $-20°$ to $20°$ C. Although the reaction time varies, depending on the reaction temperature and particular reactant and solvent used, it can range from several tens minutes to several tens hours. It is usually for 0.5–48 hours, preferably 1–24 hours.

Isolation of an object compound from the reaction mixture may be effected by any conventional technique. For example; extraction with an organic solvent such as dichloromethane, chloroform or ethyl acetate; and chromatograhy on silica gel; an ion-exchange resin; a cross-linked dextran; a high porous polymer of styrene or acrylic ester or the like.

The substituted ureidophenylacetic acid of the formula (III) is novel and may be easily prepared, for example, by reacting a corresponding α-aminophenylacetic acid with a corresponding benzoyl isocyanate or N-benzoyl-N-lower alkylcarbamoyl halide, the hydroxyl group of which are protected, and if desired, removing the protecting groups. A useful protecting group or technique for removing the group will be illustrated in detail in the explanation for a compound represented by formula (IX), particularly, groups of $R_{21}$ and $R_{32}$.

Another embodiment of this invention relates to a process for preparing a compound represented by the formula (I) wherein $R_3$ is a lower alkanoyloxy group, or its salt. More particularly, the process comprises reacting an α-aminobenzylcephalosporin of the formula

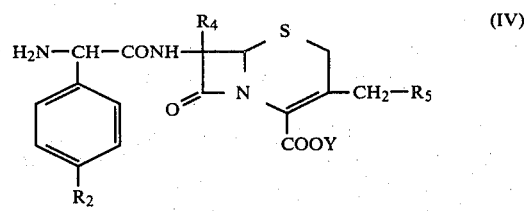

wherein $R_2$, $R_4$, $R_5$ and Y are as defined above, or its reactive derivative with an benzoyl isocyanate of the formula

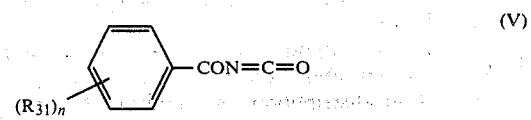

wherein n is as defined above and $R_{31}$ is a lower alkanyloxyl group, or with a carbamoyl halide of the formula

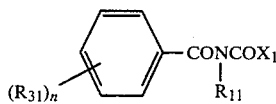

wherein n and $R_{31}$ are as defined above, $R_{11}$ is a lower alkyl group and $X_1$ is a halogen atom, and then converting Y to a hydrogen atom, if necessary.

The reactive derivative of the α-aminobenzylcephalosporin means a derivative, the α-amino group in the acyl group of which is activated into reactive form. For example, the introduction of trimethylsilyl into the amino group sufficiently causes the necessary amide-forming reaction.

When Y in the formula (IV) is a protecting group, the particular protecting group and a technique for removing the group which are useful in this process are the same as those explained as for 7-aminocephalosporin of the formula (II).

If a benzoyl isocyanate of the formula (V) is subjected to the reaction, an object compound of the formula (I) wherein $R_1$ is a hydrogen atom is produced. While, in the case of reaction with a carbamoyl halide, a compound of the formula (I) wherein $R_1$ is a lower alkyl group is produced.

The reaction is generally carried out in a solvent. The solvent which is useful in this reaction is an inert organic solvent such as dichloromethane, 1,2-dichloroethane, chloroform, acetonitrile, acetone, tetrahydrofuran, ethyl acetate, dioxane or the like. Any solvent which is miscible with water may be used as an aqueous mixture. The reaction is generally carried out under cooling or at an ambient temperature. The temperature usually ranges from −30° to 35° C., preferably from −20° to 20° C. Although the reaction time varies, depending on the reaction temperature and particular reactant and solvent used, it ranges usually from several tens minutes to 24 hours, preferably 0.5 to 5 hours.

Isolation of an object compound from the reaction mixture can be easily effected by a conventional technique described above.

Still another embodiment of this invention relates to a process for preparing a cephalosporin derivative represented by the formula (I) wherein $R_2$ is a hydrogen atom and $R_3$ is a lower alkanoyloxyl group and its salts. More particularly, the process comprises reacting an α-ureidobenzylcephalosporin of the formula

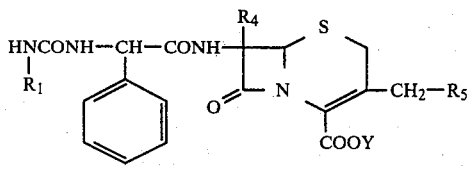

wherein $R_1$, $R_4$, $R_5$ and Y are as defined above, or its reactive derivative with a benzoyl halide of the formula

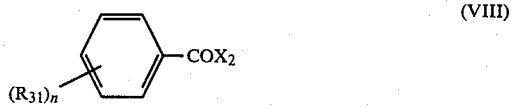

wherein n and $R_{31}$ are as defined above and $X_2$ is a halogen atom and, if necessary, converting Y to a hydrogen atom.

The reactive derivative of the α-ureidobenzylcephalosporin of the formula (VII) is a derivative, the ureido group of 7-positioned acyl group of which is activated into a reactive form.

The reaction is conveniently carried out in a solvent. The solvent which is useful in this reaction is an inert organic solvent such as chloroform, dichloromethane, tetrahydrofurna, ethyl acetate, dioxane, acetonitrile or the like. The reaction temperature ranges usually from −10° to 25° C., preferably, from 0° to 10° C. Although the reaction time varies, depending on the reaction temperature and particular reactants and solvent used it ranges usually from 1–48 hours, preferably, 1–10 hours.

Isolation of an object compound from the mixture can be easily effected by a conventional technique as explained above.

A further embodiment of this invention relates to a process for preparing a cephalosporin derivative represented by the formula (I) wherein $R_3$ is a hydroxyl group. More particularly, the process for preparing a cephalosporin derivative represented by the formula

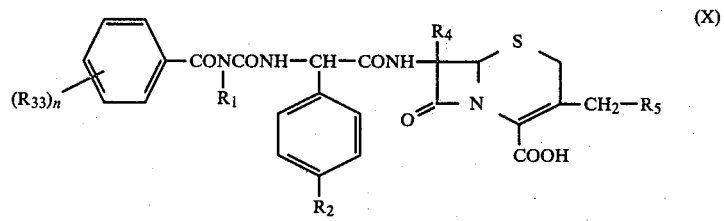

wherein $R_1$, $R_2$, $R_4$, $R_5$ and n are as defined above and $R_{33}$ is a hydroxyl group provided that the each position of substituents $R_{33}$ is the same as that for $R_{32}$ described hereunder, which comprises removing a protecting group from a compound of the formula

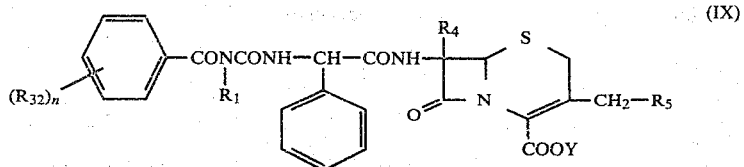

wherein $R_1$, $R_4$, $R_5$, Y and n are as defined above, $R_{21}$ is a hydrogen atom, a hydroxyl group of a protected hydroxyl group, $R_{32}$ is a hydroxyl group or a protected hydroxyl group, provided that at least two of $R_{32}$ are bonded to adjacent carbon atoms, the position of substituent $R_{32}$ being selected from 3 to 5 position when $R_1$ is a lower alkyl group, and 2 to 6 positions when $R_1$ is a hydrogen atom, and provided that at least one of $R_{21}$, $R_{32}$ and Y is a protecting group or is protected.

In the formula (IX), a hydroxyl protecting group for $R_{21}$ or $R_{32}$ is a protecting group which can be easily removed under mild conditions. Examples of such protecting group are a lower alkanoyl group such as acetyl, propionyl, butyryl or isobutyryl.

Although the removal of such lower alkanoyl group may be effected by any conventional way, it is desirable to effect the removal by the use of a base. The base which is useful in this method includes inorganic and organic bases. Examples of the inorganic base are an ammonium or alkali metal salt of a weak acid such as carbonic acid, acetic acid, phosphoric acid, etc.; an ammonium-form of weakly acidic ion-exchange resin; and ammonia. Examples of the organic base are a primary- secondary- or tertiary-amine having one to three lower alkyl groups; or hydroxyalkyl groups; and alicyclic amines such as piperidine or morpholine.

An embodiment of the removal of the protecting group comprises having a base act on a compound having the protecting group in a solvent in the presence of a substance having alcoholic hydroxyl group(s). In this embodiment, a base which is useful is an organic or inorganic base soluble in the substance having alcoholic hydroxyl group(s) and in the solvent, preferably a base containing therein at least one basic nitrogen atom, such as ammonia, propylamine, diethylamine, triethylamine, diethylaminoethanol, ethanolamine, triethanolamine, piperidine or morpholine. In addition to these bases, an ammonium form of weakly acidic ion-exchange resin may be used as a suspension in the solvent.

The substance having alcoholic hyroxyl group(s) which may be used includes alcohol such as methanol, ethanol, ethyleneglycol or glycerine; or a hydroxyl lower alkylamine such as diethylaminoethanol, ethanolamine or triethanolamine.

The solvent which can dissolve the salt of the base with the protected cephalosporin derivative and a salt of cephalosporin derivative, the object product, with the base, may be used. Examples of such solvents are aprotic polar solvents such as dimethylformamide; and non-polar solvents such as dichloromethane and chloroform. Further, among the substances having alcoholic hydroxyl group(s) may be used as a desirable solvent, provided that such substance is adapted to the requirements for the solvent as explained above, for example, methanol and glycerine.

Preferred combinations for carrying out the removal of the protecting group are methanol-ammonia, triethylamine-triethanolamine-dimethylformamide, diethylaminoethanol-dimethylformamide and the like. The amount of the base varies depending on the number of the protecting groups in the protected cephalosporin derivative and the total amount of basic substance present in the reaction system. However, the base is usually present in an amount of 1.1–30 moles, preferably, 3–20 moles per mole of the protected cephalosporin derivative.

Although such substance is usually used in a large excess amount as a solvent, it may be used in an amount of 2–30 moles per mole of the protected cephalosporin derivative when a solvent is also used. In case a triethylamine-triethanolamine-dimethylformamide system, one of the preferable combinations, is used, triethylamine is used usually in an amount of 0.1–10 moles, preferably, 2–4 moles and triethanolamine, usually 0.7–10 moles, preferably, 3–5 moles, per mole of the protected cephalosporin derivative. In case a methanol-ammonia system is used, the amount of ammonia is in the range from 1.1 to 30 moles, preferably, from 2 to 10 moles per mole of the protected cephalosporin derivative, and methanol is in an amount sufficient to act as a solvent. In case a diethylaminoethanol-dimethylformamide system is used, the amount of diethylaminoethanol is usually in the range of from 2 to 30 moles, preferably, from 5 to 20 moles per mole of the protected cephalosporin derivative and, dimethylformamide is in an amount sufficient to act as a solvent.

Although the reaction temperature varies depending on the particular substance having alcoholic hydroxyl group(s), the base and the solvent used, it is usually selected from the range of $-30°$ to 40° C. Especially, in case the substance having hydroxyl group(s) also acts as a base, the temperature is usually at 10°–40° C., preferably at 20° to 35° C. and in case the substance having hydroxyl group(s) also acts as a solvent, the temperature is usually at $-30°$ to 40° C., preferably at $-25°$ to 35° C.

The reaction time is usually for 30 minutes to 20 hours, preferably, 1 to 10 hours.

In addition to the embodiment for removing protecting groups explained above, other techniques for removing the protecting groups from the protected cephalosporin derivative may be used. One of such techniques is carried out by using a combination of a nitrogen atom-containing-base such as ammonia or primary- or secondary-lower alkylamine with an aprotic solvent such as dimethylformamide capable of dissolving the salt of the cephalosporin derivative with such bases.

Another technique is to use (a) a base such as an inorganic base such as ammonia, ammonium bicarbonate, ammonium carbonate, ammonium phosphate, ammonium acetate, sodium acetate, alkali metal bicarbonate or alkali metal carbonate; an organic base such as ethylamine, diethylamine, triethylamine, piperidine or morpholine; or an ammonium form of weakly acidic ion-exchange resin and (b) a solvent such as water or an aqueous mixture of hydrophilic aprotic solvent such as dioxane.

When Y in the formula (IX) is a protecting group, the particular protecting group and a technique for removing the group ae the same as those described in the explanation with respect to Y in the formula (II) representing 7-aminocephalosporin.

It will be easily understood that when both $R_{21}$ and $R_{31}$ are protected groups, the removal of the groups is effected by a single technique. While the removal of the protecting group for Y is accomplished by a technique different from that for $R_{21}$ or $R_{32}$. If it is necessary to remove not only a protecting group for $R_{21}$ or $R_{32}$ but also a protecting group for Y, the latter must be first removed in order to keep the cepham ring of the compound of the formula (IX) stable.

A further embodiment of this invention relates to a process for preparing a cephalosporin derivative represented by the formula (I) wherein $R_3$ is a hydroxyl group and $R_5$ is $-S-R_6$ (wherein $R_6$ is as defined in the formula (I)). More particularly, the process comprises reacting a 3-acetoxymethylcephalosporin derivative of the formula

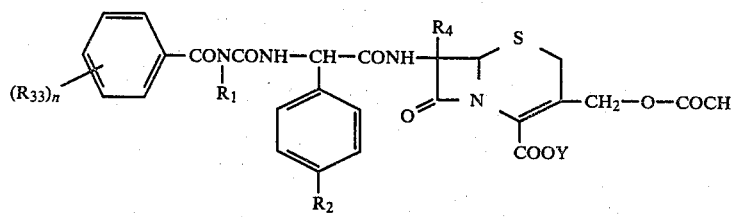
(XI)

wherein $R_1$, $R_2$, $R_4$, Y and n are as defined above and $R_{33}$ is a hydroxyl group and at least two of $R_{33}$ are bonded to adjacent carbon atoms, the position of substituent $R_{33}$ being selected from 3-5 position when $R_1$ is a lower alkyl group, and 2-6 position when $R_1$ is a hydrogen atom, with thiol or its salt of the formula

HS—$R_6$ (XII)

wherein $R_6$ is as defined for the formula (I) and, if necessary, converting Y to a hydrogen atom.

In this reaction, a thiol is generally used in the form of sodium salt or potassium salt. While, a thiol in the free form can be used in the presence of an inorganic base such as an alkali hydroxide, alkali carbonate, alkali bicarbonate, etc. or an organic base such as a trialkyl amine, etc.

The reaction is usually carried out in a solvent. The solvent which is commonly used includes acetone, methanol, ethanol, tetrahydrofuran, and the like, and may be used as an aqueous solution thereof.

The reaction is generally carried out under warming or at ambient temperature. That is, the reaction temperature is usually in the range of 20° to 70° C., preferably, 45° to 55° C. The reaction time usually ranges from 5 to 60 hours, preferably, 15 to 30 hours.

Isolation of an object compound from the reaction mixture can be easily carried out by any conventional technique.

An optical isomer such as D- or L-isomer of the object compound of the formula (I) can be prepared by using an optically active starting compound as an α-aminophenylacetic acid or a substituted ureidophenyl acetic acid which is prepared by a usual optical resolution technique, for example, the technique reported by J. P. Greenstein and M. Winitz in "Chemistry of the Amino Acids", Vol. 1, pp. 715-760, John Wiley and Sons, N.Y. (1961).

The object compound of this invention can be formulated into various pharmaceutical preparations adapted to various administration routes in a manner similar to that used for other cephalosporin compounds. Therefore, one aspect of this invention involves a pharmaceutical composition for human beings or animals. The preparation is provided by using a conventional pharmaceutical carrier, diluent and/or excipient.

In particular, an emulsion, solution or suspension in an aqueous or oily vehicle can be formulated for injection. A suppository is also provided by using a conventional suppository base such as coconut oil or other glycerides.

The content of the active compound varies depending on the administration route, but is usually above 0.1% such as 5-99%, preferably 10-60%.

The amount of administration for human being is usually in the range from 100 to 3000 mg per day for an adult. The administration in an amount ranging from 500 to 2000 mg per day is preferable for an adult though the amount varies depending on body weight, age, symton, route of administration or frequency of administration.

The process for preparing the compound of this invention is further illustrated by the following Examples.

In the Examples, the thin layer chromatography was carried out by the use of, as a carrier, silica gel 60 $F_{254}$ (a pre-coated plate manufactured by E. Merck, Darmstadt) and as developer the followings:

(I) ethyl acetate-ethanol-acetic acid (25:5:1, by volume)

(II) ethyl acetate-ethanol-acetic acid-water (10:4:2:1, by volume)

EXAMPLE 1

(1) A solution of triethylamine (6.04 g) in dried dichloromethane (20 ml) was added dropwise at room temperature to a solution of N-methyl-3,4-diacetoxybenzamide (15.0 g) and trimethylsilyl chloride (6.49 g) in dried dichloromethane (70 ml). After the mixture was refluxed for 30 minutes a solution (82 ml) of phosgene (42 ml) in dried dichloromethane was added to the mixture at a temperature of from −5° to 5° C. followed by allowing its temperature to gradually rise to room temperature. Excess phosgene and the solvent used were removed by evaporation under reduced pressure to give crude N-(3,4-diacetoxybenzoyl)-N-methylcarbamoyl chloride. The product was dissolved in cold dried dichloromethane (50 ml) and, after removing insoluble substances by filtration, made available for the subsequent reaction.

(2) N,O-Bis(trimethylsilyl)acetamide (44.3 ml) was added to a suspension of D(−)-phenylglycine (14.0 g)

in dried dichloromethane (150 ml) at room temperature followed by stirring until it became uniform. To the mixture was added dropwise the solution of N-(3,4-diacetoxybenzoyl)-N-methylcarbamoyl chloride in dried dichloromethane previously obtained in (1) while stirring. After stirring at 5° to 10° C. for 1.5 hours, the mixture was evaporated to dryness at room temperature under reduced pressure and, after adding dried methanol to the residue, the mixture was evaporated again to dryness at room temperature under reduced pressure.

Ethyl acetate (500 ml) and cold 1 N hydrochloric acid were added to the residue, and the organic layer was separated. The layer was washed with a cold, saturated sodium chloride aqueous solution (500 ml) and extracted three times with a cold, saturated sodium bicarbonate aqueous solution in a total amount of 700 ml. The aqueous layer separated was washed with ethylacetate (100 ml). The pH of the aqueous layer was adjusted to about 2.5 with cold 2 N hydrochloric acid and extracted with ethyl acetate (500 ml). The organic layer separated was washed with a cold, saturated sodium chloride aqueous solution, dried over anhydrous sodium sulfate and evaporated to dryness under reduced pressure to give 15.0 g of D(−)-α-[3-(3,4-diacetoxybenzoyl)-3-methyl-1-ureido]-α-phenylacetic acid as a white powder.

TLC: Rf 0.52, Developer (I)

IR spectrum: $\nu_{max}^{KBr}$ (cm$^{-1}$), 3,700–2,400, 1,775, 1,740, 1,700, 1,510

NMR spectrum: (DMSO-d$_6$, 60 MHz) δ(ppm) 2.29(6H,s) 3.12(3H,s), 5.35(1H,d, J=7 Hz), 7.2–7.6(8H,m), 9.65(1H,d, J=7 Hz)

The above compound was also prepared by the following method. To a mixture of tetrahydrofuran (50 ml), trimethylsilyl chloride (7 g) and D(−)-α-(3-methyl-1-ureido)phenylacetic acid (6.4 g) prepared by reacting D(−)-phenylglycine with methyl isocyanate was added dropwise triethylamine (6.4 g) at a temperature below 10° C. with stirring. After completion of the addition, the mixture was stirred at 40° to 50° C. for 1 hour and cooled to a temperature below 10° C. To the mixture was added dropwise a solution of 3,4-diacetoxybenzoyl chloride (7.9 g) in tetrahydrofuran (20 ml) and then the mixture was stirred at 50° C. for 2 hours. After cooling to a temperature below 10° C., a small amount of methanol was added to the mixture and the insoluble substances were removed by filtration. The filtrate was evaporated to dryness at room temperature under reduced pressure and the residue was purified with a column chromatography on silica gel (Wakogel C-200 manufactured by Wako Junyaku K. K., Japan) with 3–4% methanol in chloroform to give 5 g of the product as a white powder.

(3) To a solution of D(−)-α-[3-(3,4-diacetoxybenzoyl)-3-methyl-1-ureido]phenylacetic acid (2.0 g) in methanol (20 ml) was added dropwise 29% aqueous ammonia (4 ml) under cooling with ice water. The mixture was stirred for 30 minutes while allowing its temperature to gradually rise to room temperature and, then, concentrated at room temperature under reduced pressure. Ethyl acetate (100 ml) and a cold saturated sodium bicarbonate aqueous solution (70 ml) were added to the residue and the pH of the aqueous layer was adjusted to 8.5. The aqueous layer was separated and, after adjusting its pH to about 2.5 with cold 2 N hydrochloric acid, extracted with ethyl acetate (200 ml). The organic layer separated was washed with a cold, saturated sodium chloride aqueous solution, dried over anhydrous sodium sulfate, and evaporated to dryness under reduced pressure to give 1.3 g of D(−)-α-[3-(3,4-dihydroxybenzoyl)-3-methyl-1-ureido]phenylacetic acid as a white powder.

(4) D(−)-α-[3-(3,4-Dihydroxybenzoyl)-3-methyl-1-ureido]-α-phenylacetic acid (4.0 g) fully dried over phosphorus pentaoxide, was dissolved in dried tetrahydrofuran (60 ml) containing 1-hydroxybenzotriazole (1.57 g). To the solution was added dropwise 20 ml of a solution of N,N'-dicyclohexylcarbodiimide (2.87 g) in dried tetrahydrofuran at 0° C. on an ice bath under a nitrogen atmosphere. The stirring was continued while allowing its temperature to gradually rise to room temperature for 2 hours and the resulting precipitate (N,N'-dicyclohexylurea) was removed by filtration. The filtrate containing 1-benzotriazolyl ester of D(−)-α-[3-(3,4-dihydroxybenzoyl)-3-methyl-1ureido]phenylacetic acid was made available for the subsequent reaction.

(5) N,O-Bis(trimethylsilyl)acetamide (11.5 ml) was added under a nitrogen atmosphere at room temperature to a suspension of 7-amino-3-acetoxymethyl-3-cephem-4-carboxylic acid (6.32 g) in dried dichloromethane (100 ml) followed by stirring the mixture until it became uniform. To the solution was added dropwise the whole solution in tetrahydrofuran previously obtained in (4) while maintaining the temperature of the mixture between 5° and 10° C., followed by stirring for 8 hours. Then, the mixture was evaporated to dryness at room temperature under reduced pressure and, after adding dried methanol to the residue, evaporated again to dryness under reduced pressure. Ethyl acetate (100 ml) and a cold, saturated aqueous solution of sodium bicarbonate (150 ml) were added to the residue and the mixture was thoroughly stirred. After removing the undissolved substances by filtration, the pH of the filtrate was adjusted to about 1.0 with cold 2 N hydrochloric acid. The precipitate was recovered by filtration, washed with water (100 ml) and dissolved in acetone (70 ml). The solution was treated with activated charcoal and evaporated to dryness at room temperature under reduced pressure. To the residue was added acetone (5 ml) and the mixture was treated with diethyl ether (50 ml) to give 3.5 g of 7-[D(−)-α-{3-(3,4-dihydroxybenzoyl)-3-methyl-1-ureido}-α-phenylacetamido]-3-acetoxymethyl-3-cephem-4-carboxylic acid (referred to as Compound A hereunder) as a pale yellow amorphous solid.

TLC: Rf 0.45, Developer (II)

IR spectrum: $\nu_{max}^{KBr}$ (cm$^{-1}$) 3,700–2,300, 1,775, 1,675, 1,520

NMR spectrum: (DMSO-d$_6$, 60 MHz) δ(ppm) 2.02(3H,s), 3.12(3H,s), 3.47(2H,brs), 4.7–5.2(3H,m), 5.5–5.9(2H,m), 6.8–7.6(8H,m), UV spectrum: (EtOH) λmax (nm) 265, 290 (shoulder)

Color reaction with ferric chloride: positive (dark green)

(a) The procedure described above was repeated, except that the intermediate, D(−)-α-[3-(3,4-diacetoxybenzoyl)-3-methyl-1-ureido]-α-(4-hydroxyphenyl)acetic acid which has the following characteristics:

TLC: Rf 0.51, Developer (I)

IR spectrum: $\nu_{max}^{KBr}$ (cm$^{-1}$) 3,700–2,300, 1,770, 1,740, 1,700–1,680, 1,510

NMR spectrum: (DMSO-d$_6$, 60 MHz) δ(ppm) 2.2 (6H,s), 3.12(3H,s), 5.23(1H,d, J=7 Hz), 6.6–7.6(7H,m), 9.50(1H,d, J=7 Hz)

was prepared, thereby giving 7-[D(−)-α-{3-(3,4-dihydroxybenzoyl)-3-methyl-1-ureido}-α-(4-hydroxyphenyl)acetamido]-3-acetoxymethyl-3-cephem-4-carboxylic acid (referred to as Compound B hereunder) as a pale yellow amorphous solid.

TLC: Rf 0.42, Developer (II)

IR spectrum: $\nu_{max}^{KBr}$ (cm$^{-1}$) 3,700–2,300, 1,775, 1,675, 1,510

NMR spectrum: (DMSO-d$_6$, 60 MHz) δ(ppm) 2.01(3H,s), 3,19(3H,s), 3.5(2H,brs), 4.80–5.15(3H,m), 5.5–6.1(2H,m), 6.7–7.6(7H,m)

UV spectrum: (EtOH) λmax (nm) 267, 292 (shoulder)

Color reaction with ferric chloride: positive (dark green)

(b) D(−)-α-[3-(3,4-Dihydroxybenzoyl)-3-methyl-1-ureido]phenylacetic acid obtained in Example 1-(3) was reacted with 7-amino-3-(5-methyl-1,3,4-thiadiazol-2-ylthiomethyl)-3-cephem-4-carboxylic acid in a manner described above to give 7-[D(−)-α-{3-(3,4-dihydroxybenozyl)-3-methyl-1-ureido}-α-phenylacetamido]-3-(5-methyl-1,3,4-thiadiazol-2-ylthiomethyl)-3-cephem-4-carboxylic acid (referred to as Compound C hereunder) as a pale yellow amorphous solid.

TLC: Rf 0.40, Developer (II)

IR spectrum: $\nu_{max}^{KBr}$ (cm$^{-1}$) 3,700–2,300, 1,775, 1,680, 1,515

NMR spectrum: (DMSO-d$_6$, 60 MHz) δ(ppm) 2.69(3H,s), 3.19(3H,s), 3.68(2H,brs), 4.4(2H,br), 5.04(1H,d, J=5 Hz), 5.6–6.1(2H,m), 6.9–7.7(8H,m)

UV spectrum: (EtOH) λmax (nm) 272

Color reaction with ferric chloride: positive (dark green)

(c) By the procedure as described above, D(−)-α-[3-(3,4-dihydroxybenzoyl)-3-methyl-1-ureido]-α-(4-hydroxyphenyl)acetic acid was reacted with 7-amino-3-(5-methyl-1,3,4-thiadiazol-2-ylthiomethyl)-3-cephem-4-carboxylic acid to give 7-[D(−)-α-{3-(3,4-dihydroxybenzoyl)-3-methyl-1-ureido}-α-(4-hydroxyphenyl)acetamido]-3-(5-methyl-1,3,4-thiadiazol-2-ylthiomethyl)-3-cephem-4-carboxylic acid (referred to as Compound D hereunder) as a pale yellow amorphous solid.

TLC: Rf 0.39, Developer (II)

IR spectrum: $\nu_{max}^{KBr}$ (cm$^{-1}$) 3,700–2,300, 1,775, 1,680, 1,510

NMR spectrum: (DMSO-d$_6$, 60 MHz) δ(ppm) 2,70(3H,s), 3.18(3H,s), 3.7(2H,brs), 4.4(2H,br), 5.05(1H,d, J=5 Hz), 5.5–6.0(2H,m), 6.7–7.5(7H,m)

UV spectrum: (EtOH) λmax (nm) 270, 280 (shoulder)

Color reaction with ferric chloride: positive (dark green)

(d) D(−)-α-[3-(3,4-Dihydroxybenzoyl)-3-methyl-ureido]phenylacetic acid was reacted with 7-amino-3-(1-methyl-1H-tetrazol-5-ylthiomethyl)-3-cephem-4-carboxylic acid in a manner as in Example 1 to give 7-[D(−)-α-{3-(3,4-dihydroxybenzoyl)-3-methyl-1-ureido}-α-phenylacetamido]-3-(1-methyl-1H-tetrazol-5-ylthiomethyl)-3-cephem-4-carboxylic acid (referred to as Compound E hereunder) as a pale yellow amorphous solid.

TLC: Rf 0.40, Developer (II)

IR spectrum: $\nu_{max}^{KBr}$ (cm$^{-1}$) 3,700–2,300, 1,775, 1,680, 1,515

NMR spectrum: (DMSO-d$_6$, 60 MHz) δ(ppm) 3.10(3H,s), 3.6(2H,br), 3.93(3H,s), 4.31(2H,brs), 5.1(1H,d, J=5 Hz), 5.4–5.8(2H,m), 6.8–7.6(8H,m)

UV spectrum: (EtOH) λmax (nm) 265, 285 (shoulder)

Color reaction with ferric chloride: positive (dark green)

(e) By the procedure as in Example 1 above, D(−)-α-[3-(3,4-dihydroxybenzoyl)-3-methyl-1-ureido]-α-(4-hydroxyphenyl)acetic acid was reacted with 7-amino-3-(1-methyl-1H-tetrazol-5-ylthiomethyl)-3-cephem-4-carboxylic acid to give 7-[D(−)-α-{3-(3,4-dihydroxybenzoyl)-3-methyl-1-ureido}-α-(4-hydroxyphenyl)acetamido]-3-(1-methyl-1H-tetrazol-5-ylthiomethyl)-3-cephem-4-carboxylic acid (referred to as Compound F hereunder) as a pale yellow amorphous solid.

TLC: Rf 0.39, Developer (II)

IR spectrum: $\nu_{max}^{KBr}$ (cm$^{-1}$) 3,700–2,300, 1,770, 1,675, 1,510

NMR spectrum: (DMSO-d$_6$, 60 MHz) δ(ppm) 3,11(3H,s), 3,6(2H,br), 3.95(3H,s), 4.31(2H,brs), 5.1(1H,d, J=5 Hz), 5.3–5.9(2H,m), 6.5–7.5(7H,m)

UV spectrum: (EtOH) λmax (nm) 265, 280 (shoulder) 290 (shoulder)

Color reaction with ferric chloride: positive (dark green)

(f) D(−)-α-[3-(3,4-Dihydroxybenzoyl)-3-methyl-1-ureido]phenylacetic acid was reacted with 7-amino-3-(1,3,4-thiadiazol-2-ylthiomethyl)-3-cephem-4-carboxylic acid in a manner as in Example 1 to give 7-[D(−)-α-{3-(3,4-dihydroxybenzoyl)-3-methyl-1-ureido}-α-phenylacetamido]-3-(1,3,4-thiadiazol-2-ylthiomethyl)-3-cephem-4-carboxylic acid (referred to as Compound G hereunder) as a pale yellow amorphous solid.

TLC: Rf 0.40, Developer (II)

IR spectrum: $\nu_{max}^{KBr}$ (cm$^{-1}$) 3,700–2,300, 1,775 1,680, 1,520

NMR spectrum: (DMSO-d$_6$, 60 MHz) δ(ppm) 3.17(3H,s), 3.7(2H,br), 4.5(2H,br), 5.04(1H,d,J=5 Hz), 5.6–6.0(2H,m), 6.9–7.7(8H,m), 9.36(1H,s)

UV spectrum: (EtOH) λmax (nm) 268

Color reaction with ferric chloride: positive (dark green)

(g) D(−)-α-[3-(3,4-Dihydroxybenzoyl)-3-methyl-1-ureido]-α-(4-hydroxyphenyl)acetic acid was reacted as in Example 1 with 7-amino-3-(1,3,4-thiadiazol-2-ylthiomethyl)-3-cephem-4-carboxylic acid to give 7-[D(−)-α-{3-(3,4-dihydroxybenzoyl)-3-methyl-1-ureido}-α-(4-hydroxyphenyl)acetamido]-3-(1,3,4-thiadiazol-2-ylthiomethyl)-3-cephem-4-carboxylic acid (referred to as Compound H hereunder) as a pale yellow amorphous solid.

TLC: Rf 0.38, Developer (II)

IR spectrum: $\nu_{max}^{KBr}$ (cm$^{-1}$) 3,700–2,300, 1,775, 1,680, 1,510

NMR spectrum: (DMSO-d$_6$, 60 MHz) δ(ppm) 3.18 (3H,s), 3.7(2H,brs), 4.5(2H,br), 5.05(1H,d, J=5 Hz), 5.5–6.0(2H,m), 6.7–7.5(7H,m), 9.37(1H,s)

UV spectrum: (EtOH) λmax (nm) 270, 280 (shoulder)

Color reaction with ferric chloride: positive (dark green)

(h) D(−)-α-[3-(3,4-Dihydroxybenzoyl)-3-methyl-1-ureido]-α-(4-hydroxyphenyl)acetic acid was reacted as in Example 1 above with 7-amino-3-(1,2,3-triazol-5-ylthiomethyl)-3-cephem-4-carboxylic acid to give 7-[D(−)-α-{3-(3,4-dihydroxybenzoyl)-3-methyl-1-ureido}-α-(4-hydroxyphenyl)acetamido]-3-(1,2,3-triazol-5-ylthiomethyl)-3-cephem-4-carboxylic acid (referred to as Compound I hereunder) as a pale yellow powder.

TLC: Rf 0.39, Developer (II)

IR spectrum: $\nu_{max}^{KBr}$ (cm$^{-1}$) 3,700–2,300, 1,770 1,680, 1,515

NMR spectrum: (DMSO-d$_6$, 60 MHz) δ(ppm) 3.11(3H,s), 3.6(2H,brs), 3.95(2H,brs), 5.03(1H,d, J=5 Hz), 5.4–5.9(2H,m), 6.6–7.5(7H,m), 7.95(1H,s)

UV spectrum: (EtOH) λmax (nm) 272, 280 (shoulder)

Color reaction with ferric chloride: positive (dark green)

(i) D(—)-α-[3-(3,4-Diacetoxybenzoyl)-3-methyl-1-ureido]-α-(4-hydroxyphenyl)acetic acid was reacted as in Example 1 with 7-amino-3-(1,2,3-triazol-5-ylthiomethyl)-3-cephem-4-carboxylic acid to give 7-[D(—)-α-{3-(3,4-diacetoxybenzoyl)-3-methyl-1-ureido}-α-(4-hydroxyphenyl) acetamido]-3-(1,2,3-triazol-5-ylthiomethyl)-3-cephem-4-carboxylic acid (referred to as Compound J hereunder) as a pale yellow powder.

TLC: Rf 0.40, Developer (II)

IR spectrum: $\nu_{max}^{KBr}$ (cm$^{-1}$) 3,700–2,300, 1,770 1,760, 1,680, 1,510

NMR spectrum: (acetone-d$_6$, 60 MHz) δ(ppm) 2.26(6H,s), 3.20(3H,s), 3.6(2H,br), 4.1(2H,br), 5.01(1H,d, J=5 Hz), 5.5–6.0(2H,m), 6.7–7.7(7H,m), 7.86(1H,s)

UV spectrum: (EtOH) λmax (nm) 268

EXAMPLE 2

(1) Oxalyl chloride (5.3 g) was added to a solution of 2,3-diacetoxybenzamide (4.0 g) in 1,2-dichloroethane (40 ml) while stirring under cooling. The mixture was gradually heated to a reflux temperature and allowed to react under reflux for 10 hours. Then, the solvent and excess oxalyl chloride were distilled off under reduced pressure to give 2,3-diacetoxybenzoyl isocyanate, which was dissolved in dried dichloromethane (40 ml) for the subsequent reaction.

(2) N,O-Bis(trimethylsilyl)acetamide (19 ml) was added dropwise at room temperature to a suspension of D(—)-phenylglycine (5.3 g) in dried dichloromethane (100 ml) at room temperature followed by stirring until the mixture was made uniform. The solution previously obtained in (1) above was added dropwise to the clear solution at a temperature of from 5° to 10° C. After stirring the mixture for 1.5 hours at the same temperature, the mixture was evaporated to dryness at room temperature under reduced pressure. To the residue was added dried methanol and evaporated to dryness under reduced pressure. To the residue was added cold diluted aqueous hydrochloric acid (200 ml) and the mixture was stirred for 5 to 10 minutes. The resulting white precipitates were collected by filtration and dissolved in a cold, saturated sodium bicarbonate aqueous solution (250 ml), and the insoluble sobtances were removed by filtration. The filtrate was washed with ethyl acetate (250 ml) and, after adjusting its pH to about 1 with cold 2 N hydrochloric acid, the resulting white precipitates were collected by filtration, washed with water and then diethyl ether, and dried in air to give 4.5 g of D(—)-α-[3-(2,3-diacetoxybenzoyl)-1-ureido]phenylacetic acid as a white powder. m.p. 200°–201° C. (decomposition).

Analysis: Calcd. for C$_{20}$H$_{18}$N$_2$O$_8$: C, 57,97; H, 4.38; N, 6.76(%). Found: C, 57.64; H, 4.39; N, 6.65(%).

(3) D(—)-α-[3-(2,3-Diacetoxybenzoyl)-1-ureido]-phenylacetic acid (2.0 g) was suspended in methanol (20 ml) and to the solution was added dropwise 29% aqueous ammonia (2.5 ml) under cooling with ice-water. The mixture was stirred at 5° to 10° C. for 30 minutes and concentrated at room temperature under reduced pressure. To the residue were added ethyl acetate (50 ml) and a cold, saturated sodium bicarbonate aqueous solution (100 ml). The aqueous layer was separated and, after removal of the insoluble substances by filtration, its pH was adjusted to about 2.5 with cold 2 N hydrochloric acid. The resulting white precipitate was collected by filtration, washed with water and then diethyl ether, and dried in air to give 1.4 g of D(—)-α-[3-(2,3-dihydroxybenzoyl)-1-ureido]phenylacetic acid as a white powder. m.p. 211°–212° C. (decomposition).

Analysis: Calcd. for C$_{16}$H$_{14}$N$_2$O$_6$.H$_2$O: C, 55.17; H, 4.63; N, 8.04(%). Found: C, 55.44; H, 4.38; N, 8.08(%).

(4) D(—)-α-[3-(2,3-Dihydroxybenzoyl)-1-ureido]-phenylacetic acid (4.00 g) and 1-hydroxybenzotriazole (1.63 g) were dissolved in dried tetrahydrofuran (100 ml) and to the solution was added dropwise at 0° to 5° C. a solution of N,N'-dicyclohexylcarbodiimide (2.99 g) in dried tetrahydrofuran (20 ml). The mixture was stirred while allowing its temperature to gradually rise to room temperature and, about 2.5 hours after, the precipitating dicyclohexylurea was removed by filtration. The filtrate containing 1-benzotriazolyl ester of D(—)-α-[3-(2,3-dihydroxybenzoyl)1-ureido]phenylacetic acid was used for the subsequent reaction.

(5) N,O-Bis(trimethylsilyl)acetamide (7.8 ml) was added at room temperature to a suspension of 7-amino-3-(1-methyl-1H-tetrazol-5-ylthiomethyl)-3-cephem-4-carboxylic acid (5.2 g) in dried dichloromethane (200 ml) followed by stirring until the mixture was made uniform. To the uniform mixture was added dropwise the tetrahydrofuran solution previously obtained in (4) above while maintaining its temperature at 5°–10° C. with stirring to form a precipitate. N,O-Bis(trimethylsilyl)acetamide was added again until the mixture became uniform and then the stirring was continued at the same temperature for 8 hours. Then, the mixture was evaporated to dryness at room temperature under reduced pressure and, after adding dried methanol to the residue, the mixture was evaporated again to dryness under reduced pressure. To the residue were added ethyl acetate (200 ml) and a cold, saturated sodium bicarbonate aqueous solution (200 ml) followed by thoroughly stirred. After removing the undissolved substances by filtration, the pH of the aqueous layer was adjusted to about 1.0 with cold 2 N hydrochloric acid. The precipitates were recovered by filtration, washed with water (100 ml) and dissolved in acetone (150 ml). The solution was treated with activated charcoal and evaporated to dryness at room temperature under reduced pressure. The residue was treated with diethyl ether (70 ml) to give 4.0 g of 7-[D(—)-α-{3-(2,3-dihydroxybenzoyl)-1-ureido}-α-phenylacetamido]-3-(1-methyl-1H-tetrazol-5-ylthiomethyl)-3-cephem-4-carboxylic acid (referred to as Compound K hereunder) as a pale yellow powder.

TLC: Rf 0.38, Developer (II)

IR spectrum: $\nu_{max}^{KBr}$(cm$^{-1}$) 3,700–2,300, 1,775, 1,680, 1,530, 1,490

NMR spectrum: (acetone-d$_6$, 60MHz) δ(ppm), 3.7(2H,br), 3.96(3H,s), 4.37(2H,brs), 5.05(1H,d, J=5Hz), 5.6–6.0(2H,M), 6.8–7.7(8H,m)

UV spectrum: (EtOH) λmax (nm) 256, 280 (shoulder), 310 (shoulder)

Color reaction with ferric chloride: positive (dark green)

(a) The procedure described in Example 2-(1), (2), (3) and (4) was repeated, except that 3,4-diacetoxybenzamide was used instead of 2,3-diacetoxybenzamide used in (1) above to give 1-benzotriazolyl ester of D(—)-α-[3-(3,4-dihydroxybenzoyl)-1-ureido]-α-phenylacetic acid. The ester was reacted with 7-amino-3-(5-methyl-1,3,4-thiadiazol-2-ylthiomethyl)-3-cephem-4-carboxylic acid and treated as in Example 2-(5) to give 7-[D(—)-α-{3-(3,4-dihydroxybenzoyl)-1-ureido}-α-phenylacetamido]-

3-(5-methyl-1,3,4-thiadiazol-2-ylthiomethyl)-3-cephem-4-carboxylic acid (referred to as Compound L hereunder) as a pale yellow powder.

TLC: Rf 0.36, Developer (II)

IR spectrum: $\nu_{max}^{KBr}$ (cm$^{-1}$) 3,700–2,200, 1,770, 1,675, 1,525

NMR spectrum: (acetone-d$_6$, 60 MHz) δ(ppm) 2.69(3H,s), 3.72(2H,brs), 4.4(2H,br), 5.13(1H,d, J=5 Hz), 5.5–5.9(2H,m), 6.8–7.7(8H,m)

UV spectrum: (EtOH) νmax (nm) 268, 290 (shoulder)

Color reaction with ferric chloride: positive (dark green)

(b) D(−)-α-[3-(2,3-Diacetoxybenzoyl)-1-ureido]-α-phenylacetic acid obtained in Example 2-(2) was reacted with 7-amino-3-(1-methyl-1H-tetrazole-5-ylthiomethyl)-3-cephem-4-carboxylic acid as in Example 2-(4) and (5) to give 7-[D(−)-α-{3-(2,3-diacetoxybenzoyl)-1-ureido}-α-phenylacetamido]-3-(1-methyl-1H-tetrazol-5-ylthiomethyl)-3-cephem-4-carboxylic acid (referred to as Compound M hereunder) as a pale yellow powder.

IR spectrum: $\nu_{max}^{KBr}$ (cm$^{-1}$) 3,700–2,300, 1,775, 1,690, 1,530, 1,490

NMR spectrum: (acetone-d$_6$, 60 MHz) δ(ppm) 2.28(6H,s), 3.75(2H,brs), 3.95(3H,s), 4.4 (2H,brs), 5.07(1H,d, J=5 Hz), 5.6–6.0(2H,m), 7.2–8.0(8H,m)

EXAMPLE 3

(1) Triethylamine (10.2 g) was added dropwise to a suspension of 7-amino-3-acetoxymethyl-3-cephem-4-carboxylic acid (8.2 g) in dried dichloromethane (80 ml) at room temperature followed by stirring the mixture for 30 minutes at the same temperature. The mixture obtained was used for subsequent reactions.

(2) D(−)-α-[3-(3,4-Diacetoxybenzoyl)-3-methyl-1-ureido]phenylacetic acid (8.6 g) obtained by Example 1-(2) and pivaloyl chloride (3.0 g) were dissolved in dried dichloromethane (40 ml) and to the solution was added dropwise triethylamine (2.4 g) at a temperature below −15° C. After stirring the solution at the same temperature for one hour, the dichloromethane solution previously prepared by (1) above was added dropwise to the solution at a temperature below −10° C. followed by stirring for 1–1.5 hours at the same temperature. The solution was evaporated to dryness under reduced pressure and ethyl acetate (200 ml) and a cold, saturated sodium bicarbonate aqueous solution (200 ml) were added to the residue. After removing the undissolved substances by filtration, the pH of the aqueous layer was adjusted to about 1.0 with use of cold 2 N hydrochloric acid and extracted with ethyl acetate (200 ml). The recovered organic layer was washed with a cold, saturated sodium chloride aqueous solution, dried over anhydrous magnesium sulfate and distilled under reduced pressure to remove the solvent used. The residue was subjected to a column chromatography using a column filled with Diaion HP-20 (Trade name of a resin useful for reversed phase chromatography, manufactured by Mitsubishi Kasei Kogyo Kabushiki Kaisha, Japan). The fractions eluted with methanol-water (3:1 by volume) were collected and distilled under reduced pressure to remove the solvent used to give 7.0 g of 7-[D(−)-α-{3-(3,4-diacetoxybenzoyl)-3-methyl-1-ureido{-α-phenylacetamido}-3-acetoxymethyl-3-cephem-4-carboxylic acid (referred to as Compound N hereunder) as white powder.

TLC: Rf 0.62, Developer (II)

IR spectrum: $\nu_{max}^{KBr}$ (cm$^{-1}$) 3,700–2,300, 1,780, 1,745, 1,695, 1,510

NMR spectrum: (acetone-d$_6$, 60 MHz)δ(ppm) 2.00(3H,s) 2.28(6H,s), 3.15(3H,s), 3.5(2H,brs), 4.6–5.3(3H,m), 5.5–6.0(2H,m), 7.2–7.7(8H,m)

(a) By the procedure as in Example 3,7-amino-3-acetoxymethyl-3-cephem-4-carboxylic acid which was used after silylation by reacting with N,O-bis(trimethylsilyl)acetamide, was reacted with D(−)-α-{3-(3,4-diacetoxybenzoyl)-3-methyl-1-ureido]-α-(4-hydroxyphenyl)acetic acid obtained by Example 1(a) and treated to give 7-[D(−)-α-[3-(3,4-diacetoxybenzoyl)-3-methyl-1-ureido]-α-(4-hydroxyphenyl)acetamido]-3-acetoxymethyl-3-cephem-4-carboxylic acid (referred to as Compound O hereunder) as white powder. The purification was effected by column chromatography using sillica gel instead of Diaion HP-20 and eluting with methanol-chloroform (1:20 by volume).

TLC: Rf 0.54, Developer (II)

IR spectrum: $\nu_{max}^{KBr}$ (cm$^{-1}$) 3,700–2,300, 1,775, 1,740–1,670, 1,510

NMR spectrum: (acetone-d$_6$, 60 MHz) δ(ppm) 2.00(3H,s), 2.28(6H,s), 3.16(3H,s), 3.5(2H,brs), 4.6–5.3(3H,m), 5.5–6.1(2H,m), 6.7–7.7(7H,m)

(b) By the procedure described in Example 3-(1) and (2), D(−)-α-[3-(3,4-diacetoxybenzoyl)-3-methyl-1-ureido]phenylacetic acid and 7-amino-3-(5-methyl-1,3,4-thiadiazol-2-ylthiomethyl)-3-cephem-4-carboxylic acid were treated to give 7-[D(−)-α-[3-(3,4-diacetoxybenzoyl-3-methyl-1-ureido}-α-phenylacetamido]-3-(5-methyl-1,3,4-thiadiazol-2-ylthiomethyl)-3-cephem-4-carboxylic acid (referred to as Compound P hereunder) as a pale yellow powder.

TLC: Rf 0.50, Developer (II)

IR Spectrum: $\nu_{max}^{KBr}$ (cm$^{-1}$) 3,700–2,300, 1,775, 1,690, 1,510

NMR spectrum: (acetone-d$_6$, 60 MHz) δ(ppm) 2.28(6H,s), 2.67(3H,s), 3.15(3H,s), 3.74(2H,brs), 4.44(2H,AB$_q$), 5.12(1H,d, J=5 Hz), 5.6–6.0(2H,m), 7.2–7.7(8H,m)

(c) By the procedure described in Example 3(a) above, D(−)-α-[3-(3,4-diacetoxybenzoyl)-3-methyl-1-ureido]-α-(4-hydroxyphenyl)acetic acid and 7-amino-3-(5-methyl)-1,3,4-thiadiazol-2-ylthiomethyl)-3-cephem-4-carboxylic acid were treated to give 7-[D(−)-α-{3-(3,4-diacetoxybenzoyl)-3-methyl-1-ureido}-α-(4-hydroxyphenyl)acetamido]-3-(5-methyl-1,3,4-thiadiazol-2-ylthiomethyl)-3-cephem-4-carboxylic acid (referred to as Compound Q hereunder) as a white powder.

TLC: Rf 0.48, Developer (II)

IR spectrum: $\nu_{max}^{KBr}$ (cm$^{-1}$) 3,700–2,300, 1,775, 1,685, 1,510

NMR spectrum: (acetone-d$_6$, 60 MHz) δ(ppm) 2.28(6H,s), 2.68(3H,s), 3.14(3H,s), 3.65(2H,brs), 4.41(2H,AB$_q$), 5.03(1H,d, J=5 Hz), 5.5–6.0(2H,m), 6.6–7.6(7H,m)

(d) By the procedure described in Example 3-(1) and (2), D(−)-α-[3-(3,4-diacetoxybenzoyl)-3-methyl-1-ureido]phenylacetic acid and 7-amino-3-(1-methyl-1H-tetrazol-5-ylthiomethyl)-3-cephem-4-carboxylic acid were treated to give 7-[D(−)-α-{3-(3,4-diacetoxybenzoyl)-3-methyl-1-ureido}-α-phenylacetamido]-3-(1-methyl-1H-tetrazol-5-ylthiomethyl)-3-cephem-4-carboxylic acid (referred to as Compound R hereunder) as a white powder.

TLC: Rf 0.55, Developer (II)

IR spectrum: $\nu_{max}^{KBr}$ (cm$^{-1}$) 3,700–2,300, 1,775, 1,690, 1,510

NMR spectrum: (acetone-d$_6$, 60 MHz) δ(ppm) 2.27(6H,s), 3.13(3H,s), 3.75(2H,brs), 3.93(3H,s), 4.37(2H,brs), 5.11(1H,d, J=5 Hz), 5.6–5.9(2H,m), 7.2–7.7(8H,m)

(e) By the procedure described in Example 3(a), D(−)-α-[3-(3,4-diacetoxybenzoyl)-3- methyl-1-ureido]-α-(4-hydroxyphenyl) acetic acid and 7-amino-3-(1-methyl-1H-tetrazol-5-ylthiomethyl)-3-cephem-4-carboxylic acid were treated to give 7-[D(−)-α-{3-(3,4-diacetoxybenzoyl)-3-methyl-1-ureido}-α-(4-hydroxyphenyl) acetamido]-3-(1-methyl-1H-tetrazol-5-ylthiomethyl)-3-cephem-4-carboxylic acid (referred to as a Compound S hereunder) as white powder.

TLC: Rf 0.52, Developer (II)

IR spectrum: $\nu_{max}^{KBr}$ (cm$^{-1}$) 3,700–2,300 1,775, 1,690, 1,510

NMR spectrum: (acetone-d$_6$, 60 MHz) δ(ppm) 2.29(6H,s), 3.17(3H,s), 3.8(2H,br), 3.98(3H,s), 4.40(2H,brs), 5.09(1H,d, J=5 Hz), 5.4–6.0(2H,m), 6.7–7.7(7H,m)

EXAMPLE 4

Pivaloyl chloride (1.14 g) was added dropwise to a solution of D(−)-α-[3-(3,4-dihydroxybenzoyl)-3-methyl-1-ureido]-phenylacetic acid (3.25 g) obtained by Example 1-(3) and dried pyridine (0.90 g) in dried ethyl acetate (100 ml) at a temperature of from −10° to −15° C. and the mixture was stirred at the same temperature for 15 minutes. To the mixture was added dropwise a solution of 7β-amino-7α-methoxy-3-(1-methyl-1H-tetrazol-5-ylthiomethyl)-3-cephem-4-carboxylic acid benzhydryl ester (3.3 g) in dried dichloromethane (35 ml) at a temperature of from −10° to −15° C. and the mixture was stirred at the same temperature for 2 hours, at 0°–10° C. for 2 hours and then at room temperature for one hour, and evaporated under reduced pressure to dryness. The residue was dissolved in a mixture of 50 ml of water and 50 ml of ethyl acetate and the pH of the solution was adjusted to about 1.5 with 2 N hydrochloric acid. The ethyl acetate layer recovered was washed with a cold, saturated sodium bicarbonate aqueous solution and then with a cold, saturated sodium chloride aqueous solution, dried over anhydrous magnesium sulfate and distilled under reduced pressure to remove the solvent used. The residue was subjected to column chromatography with use of silica gel and the fractions eluted with ethyl acetate-benzene (1:1 by volume) were collected and distilled under reduced pressure to remove the eluting solvent to give 3.30 g of 7β-[D(−)-α-{3-(3,4-dihydroxybenzoyl)-3-methyl-1-ureido}-α-phenylacetamido]-7α-methoxy-3-(1-methyl-1H-tetrazol-5-ylthiomethyl)-3-cephem-4-carboxylic acid benzhydryl ester as a pale yellow powder. The product (0.50 g) was dissolved in dried dichloromethane (3 ml). To the solution were added anisole (1.5 ml) and trifluoroacetic acid (3.0 ml) while cooling with ice-water and, after mixing at 0°–5° C. for 30 minutes, the mixture was concentrated under reduced pressure to dryness. The residue was treated with diethyl ether to give 7β-[D(−)-α-}3-(3,4-dihydroxybenzoyl)-3-methyl-1-ureido}-α-phenylacetamido]-7α-methoxy-3-(1-methyl-1H-tetrazol-5-ylthiomethyl)-3-cephem-4-carboxylic acid (referred to as Compound T hereunder) as a pale yellow powder.

TLC: Rf 0.51, Developer (II)

IR spectrum: $\nu_{max}^{KBr}$ (cm$^{-1}$) 3,700–2,300, 1,775, 1,680, 1,515

NMR spectrum: (acetone-d$_6$, 60 MHz) δ(ppm) 3.18 (3H,s), 3.49(3H,s), 3.5(2H,brs), 3.94(3H,s), 4.37(2H,ABq), 5.03(1H,s), 5.70(1H,d, J=7 Hz), 6.9–7.7(8H,m), 8.6(1H,s), 9.90(1H,d, J=7 Hz)

UV spectrum: (EtOH) $\nu$max (nm) 272, 290 (shoulder)

Color reaction with ferric chlorde: positive (dark green)

(a) By the procedure described in Example 4 above, D(−)-α-[3-(3,4-dihydroxybenzoyl)-3-methyl-1-ureido]-phenylacetic acid and 7β-amino-7α-methoxy-3-(5-methyl-1,3,4-thiadiazol-2-ylthiomethyl)-3-cephem-4-carboxylic acid benzhydryl ester were treated to give 7β-[D(−)-α-{3-(3,4-dihydroxybenzoyl)-3-methyl-1-ureido}-α-phenylacetamido]-7α-methoxy-3-(5-methyl-1,3,4-thiadiazol-2-ylthiometyl)-3-cephem-4-carboxylic acid (referred to as Compound U hereunder) as a pale yellow powder.

TLC: Rf 0.52, Developer (II)

IR spectrum: $\nu_{max}^{KBr}$ (cm$^{-1}$) 3,700–2,300, 1,775, 1,680, 1,515

Color Reaction with ferric chloride: positive (dark green)

(b) By the procedure described above, D(−)-α-[3-(3,4-dihydroxybenzoyl)-3-methyl-1-ureido]phenylacetic acid and 7β-amino-7α-methoxy-3-(1,3,4-thiadiazol-2-ylthiomethyl)-3-cephem-4-carboxylic acid benzhydryl ester were treated to give 7β-[D(−)-α-{3-(3,4-dihydroxybenzoyl)-3-methyl-1-ureido}-α-phenylacetamideo]-7α-methoxy-3-(1,3,4-thiadiazol-2-ylthiomethyl)-3-cephem-4-carboxylic acid (referred to as Compound V hereunder) as a pale yellow powder.

TLC: Rf 0.52, Developer (II)

IR spectrum: $\nu_{max}^{KBr}$ (cm$^{-1}$) 3,700–2,300, 1,775, 1,680, 1,520

Color reaction with ferric chloride: positive (dark green)

EXAMPLE 5

Dried dichloromethane (10 ml) containing ethyl chlorocarbonate (0.35 g) and dried dichloromethane (10 ml) containing N-methylmorpholine (0.32 g) were added dropwise in the order to a solution of D(−)-α-[3-(3,4-diacetoxybenzoyl)-3-methyl-1-ureido]phenylacetic acid (1.38 g) obtained in Example 1-(2) above in dried dichloromethane (30 ml) at a temperature ranging from −20° to −15° C., followed by stirring at a temperature of from −10° to −15° C., for one hour. After adding dropwise a solution of 7β-amino-3-acetoxymethyl-7α-methoxy-3-cephem-4-carboxylic acid benzhydryl ester (1.50 g) in dried dichloromethane (10 ml) to the solution at a temperature ranging from −10° to −15° C., the mixture was stirred at the same temperature for 2 hours, at 0°–10° C. for one hour, and, then, at room temperature for one hour, and evaporated under reduced pressure to dryness. The residue was dissolved in a mixed solvent of water (50 ml) and ethyl acetate (50 ml) and its pH was adjusted to about 1.5 with 2 N hydrochloric acid while cooling with ice-water. The ethyl acetate layer recovered was washed with first a cold, saturated sodium bicarbonate aqueous solution and then with a cold, saturated sodium chloride aqueous solution, dried over anhydrous magnesium sulfate and distilled under reduced pressure to remove the solvent used. The residue was subjected to column chromatography with use of silica gel and the fractions eluted with ethyl acetate-benzene (1:2 by volume) were collected and evaporated under reduced pressure to remove the eluting solvent to give 1.52 g of 7β-[D(—)-α-{3-(3,4-diacetoxybenzoyl)-3-methyl-1-ureido}-α-phenylacetamido]-7α-methoxy-3-acetoxymethyl-3-cephem-4-carboxylic acid benzhydryl ester as a pale yellow powder.

IR spectrum: $\nu_{max}^{KBr}$ (cm$^{-1}$) 3,300, 1,775, 1,740–1,680, 1,510–1,490

NMR spectrum: (CDCl$_3$, 60 MHz) α(ppm) 2.01(3H,s), 2.28 (6H,s), 3.19(3H,s), 3.2(2H,brs), 3.51 (3H,s), 4.89(2H,ABq), 5.02(1H,s), 5.62 (1H,d, J=7 Hz), 6.90(1H,s), 7.0–7.7 (19H, brs), 9.97(1H,d J=7 Hz)

(2) Anisole (1.5 ml) and trifluoroacetic acid (3.0 ml) were added to a solution of 7β-[D(—)-α-{3-(3,4-diacetoxybenzoyl)-3-methyl-1-ureido}-α-phenylacetamido]-7α-methoxy-3-acetoxymethyl-3-cephem-4-carboxylic acid benzhydryl ester (0.40 g) obtained by (1) above in dried dichloromethane (3 ml) while cooling with ice-water, and the mixture was stirred at 0°–5° C. for 30 minutes and concentrated under reduced pressure. The residue was treated with diethyl ether to give 0.22 g of 7β-[D(—)-α-{3-(3,4-diacetoxybenzoyl)-3-methyl-1-ureido}-α-phenylacetamido]-7α-methoxy-3-acetoxymethyl-3-cephem-4-carboxylic acid (referred to as Compound Z hereunder) as a pale yellow powder.

TLC: Rf 0.60, Developer (II)

IR spectrum: $\nu_{max}^{KBr}$ (cm$^{-1}$) 3,700–2,300, 1,775, 1,740–1,680, 1,505

NMR spectrum: (acetone-d$_6$, 60 MHz) δ(ppm) 2.01 (3H,s), 2.28(6H,s), 3.17(3H,s), 3.2(2H,brs), 3.50(3H,s), 4.91(2H,ABq), 5.09(1H,s), 5.72(1H,d, J=7 Hz), 7.2–7.7(8H, m), 8.60(1H,s), 9.85(1H,d, J=7 Hz)

(a) By the procedure described in Example 5—(1) above, D(—)-α-[3-(3,4-diacetoxybenzoyl)-3-methyl-1-ureido]phenylacetic acid obtained by Example 1-(2) and 7β-amino-7α-metoxy-3-(1-methyl-1H-tetrazol-5-ylthiomethyl)-3-cephem-4-carboxylic acid benzhydryl ester were treated to give 7β-[D(—)-α-}3-(3,4-diacetoxybenzoyl)-3-methyl-1-ureido}-α-phenylacetamido]-7α-methoxy-3-(1-methyl-1H-tetrazol-5-ylthiomethyl)-3-cephem-4-carboxylic acid benzhydryl ester as a pale yellow foamed solid.

IR spectrum: $\nu_{max}^{KBr}$ (cm$^{-1}$)3,400, 1,775, 1,730–1,690, 1,510–1,490

NMR spectrum: (CDCl$_3$, 60 MHz) δ(ppm) 2.28(6H,s), 3.17(3H,s), 3.50(3H,s), 3.74(3H,s), 3.8(2H,brs), 4.3(2H,br), 5.01(1H,s), 5.67(1H,d, J=7 Hz), 6.89(1H,s), 7.1–7.7(19H,brs), 9.99(1H,d, J=7 Hz)

The obtained 7β-[D(—)-α-{3-(3,4-diacetoxybenzoyl)-3-methyl-1-ureido}-α-phenylacetamido]-7α-methoxy-3-(1-methyl-1H-tetrazol-5-ylthiomethyl)-3-cephem-4-carboxylic acid benzhydryl ester was treated as in Example 5-(2) to give 7β-[D(—)-α-{3-(3,4-diacetoxybenzoyl)-3-methyl-1-ureido}-α-phenylacetamido]-7α-methoxy-3-(1-methyl-1H-tetrazol-5-ylthiomethyl)-3-cephem-4-carboxylic acid (referred to as Compound AA hereunder) as a pale yellow powder.

TLC: Rf 0.54, Developer (II)

IR spectrum: $\nu_{max}^{KBr}$ (cm$^{-1}$) 3,700–2,300, 1,775, 1,720–1,680, 1,510

NMR spectrum: (acetone-d$_6$, 60 MHz) δ(ppm) 2.28 (6H,s), 3.16(3H,s), 3.48(3H,s), 3.8(2H,brs), 3.94(3H,s), 4.36(2H,ABq), 5.03(1H,s), 5.70(1H,d, J=7 Hz), 7.2–7.6(8H,m), 8.6(1H,s), 9.82(1H,d, J=7 Hz)

EXAMPLE 6

N,O-Bis(trimethylsilyl)acetamide (4.3 ml) was added to a suspension of 7-[D(—)-α-amino-α-(4-hydroxyphenyl) acetamido]-3-(1,2,3-triazol-5-ylthiomethyl)-3-cephem-4-carboxylic acid (4.0 g) in dried dichloromethane (50 ml) at room temperature and stirring was continued until the mixture became uniform. To the mixture was added dropwise a solution (30 ml) of N-(3,4-diacetoxybenzoyl)-N-methylcarbamoyl chloride (2.8 g) in dried dichloromethane obtained in Example 1-(1) while stirring. After stirring at 5°–10° C. for 1.5 hours, the mixture was evaporated at room temperature under reduced pressure to dryness. Dried methanol was added to the residue and the mixture was evaporated again under reduced pressure to dryness. Ethyl acetate (150 ml) and a cold, saturated sodium bicarbonate aqueous solution (150 ml) were added to the residue and the mixture was thoroughly stirred while cooling with ice-water. After removing the undissolved substances, the aqueous layer was recovered and its pH was adjusted to about 1 with cold 2 N hydrochloric acid. The precipitate was recovered by filtration, washed with water (100 ml) and dissolved in acetone (100 ml). The acetone solution was treated with activated charcoal and distilled under reduced pressure to remove the solvent used. The treatment of the residue with diethyl ether (100 ml) gave 4.5 g of Compound J.

(a) By the procedure described in this Example 6, Compound S was prepared from 7-[D(—)-α-amino-α-(4-hydroxyphenyl)acetamido]-3-(1-methyl-1H-tetrazol-5-ylthiomethyl)-3-cephem-4-carboxylic acid.

(b) By the procedure described above, Compound N was prepared from 7(D(—)-α-amino-α-phenylacetamido)-3-acetoxymethyl-3-cephem-4-carboxylic acid.

(c) By the procedure described above, Compound O was prepared from 7-[D(—)-α-amino-α-(4-hydroxyphenyl)acetamido]-3-acetoxymethyl-3-cephem-4-carboxylic acid.

(d) By the procedure described above, Compound P was prepared from 7-(D(—)-α-amino-α-phenylacetamido)-3-(5-methyl-1,3,4-thiadiazol-2-ylthiomethyl)-3-cephem-4-carboxylic acid.

(e) By the procedure described above, Compound Q was prepared from 7-[D(—)-α-amino-α-(4-hydroxyphenyl)acetamido]-3-(5-methyl-1,3,4-thiadiazol-2-ylthiomethyl)-3-cephem-4-carboxylic acid.

(f) By the procedure described above, Compound R was prepared from 7-(D(—)-α-amino-α-phenylacetamido)-3-(1-methyl-1H-tetrazol-5-ylthiomethyl)-3-cephem-4-carboxylic acid.

(g) By the procedure described above, Compound Z was prepared from 7β-(D(—)-α-amino-α-phenylacetamido)-7α-methoxy-3-acetoxymethyl-3-cephem-4-carboxylic acid.

(h) By the procedure described above, Compound AA was prepared from 7β-(D(—)-α-amino-α-phenylacetamido)-7α-methoxy-3-(1-methyl-1H-tetrazol-5-ylthiomethyl)-3-cephem-4-carboxylic acid.

EXAMPLE 7

N,O-Bis(trimethylsilyl)acetamide (20 ml) was added dropwise to a suspension of 7-(D(—)-α-amino-α-phenylacetamido)-3-(1-methyl-1H-tetrazol-5-ylthiomethyl)-3-cephem-4-carboxylic acid (12.0 g) in dried dichloromethane (200 ml) at room temperature and the stirring was continued until the mixture became uniform. To the mixture was added dropwise a solution of 2,3-diacetoxybenzoyl isocyanate obtained by Example 2-(1) in dried dichloromethane while stirring at 5°–10° C. After stirring the mixture at the same temperature for 2 hours, the mixture was evaporated at room temperature under reduced pressure to dryness and, after adding dried methanol to the residue, the mixture was evaporated again under reduced pressure to dryness. A mixture of ethyl acetate (250 ml) and a cold, saturated sodium bicarbonate solution (300 ml) was added to the residue and the mixture was thoroughly stirred while cooling with ice-water. After removing the undissolved substances, the aqueous layer was recovered and its pH was adjusted to about 1 with cold 2 N hydrochloric acid. The precipitate was recovered by filtration, washed with water (100 ml) and dissolved in acetone (150 ml). The solution was treated with activated charcoal and distilled under reduced pressure to remove the solvent used. The treatment of the residue with diethyl ether (100 ml) gave 7 g of Compound M as a pale yellow powder.

EXAMPLE 8

7-[D(—)-α-(3-Methyl-1-ureido)-α-phenylacetamido]-3-(5-methyl-1,3,4-thiadiazol-2-ylthiomethyl)-3-cephem-4-carboxylic acid (4 g) which had been prepared by reacting one molar equivalent of 7(D(—)-α-amino-α-phenylacetamido)-3-(5-methyl-1,3,4-thiadiazol-2-ylthiomethyl)-3-cephem-4-carboxylic acid with 1.2 molar equivalents of methyl isocyanate, was suspended in dichloromethane (80 ml). N,O-Bis(trimethylsilyl)acetamido (7.5 ml) was added dropwise to the suspenson at 5°–10° C., followed by stirring to make the mixture uniform. To the mixture was added a solution (10 ml) of 3,4-diacetoxybenzoyl chloride (1.9 g) in dried dichloromethane and the mixture was stirred at room temperature for 5 hours. The mixture was then evaporated at room temperature under reduced pressure to dryness and, after adding dried methanol to the residue, the mixture was evaporated again under reduced pressure to dryness. A mixture of ethyl acetate (150 ml) and a cold, saturated sodium bicarbonate aqueous solution (200 ml) was added to the mixture and the mixture was thoroughly stirred while cooling with ice-water. After removing the undissolved substances, the aqueous layer was recovered and its pH was adjusted to about 1 with cold 2 N hydrochloric acid. The precipitate was recovered by filtration, washed with water (100 ml) and dissolved in acetone (100 ml). The solution was treated with activated charcoal and evaporated under reduced pressure to remove the solvent used. The residue was dissolved in methanolchloroform, subjected to column chromatography with use of a column charged with silica gel and then eluted with the same mixed solvent. The fractions eluted were collected and distilled under reduced pressure to remove the solvent. The residue was treated with diethyl ether (50 ml) to give 3.5 g of Compound P as a white powder.

(a) By the procedure described above in this Example, 2,3-diacetoxybenzoyl chloride and 7-(D(—)-α-ureido-α-phenylacetamido)-3-(1-methyl-1H-tetrazol-5-ylthiomethyl)-3-cephem-4-carboxylic acid were treated to give Compound M.

(b) By the procedure described above, 3,4-diacetoxybenzoyl chloride and 7-[D(—)-α-(3-methyl-1-ureido)-α-phenylacetamido]-3-acetoxymethyl-3-cephem-4-carboxylic acid were treated to give Compound N.

(c) By the procedure described above, 7-[D(—)-α-(3-methyl-1-ureido)-α-phenylacetamido]-3-(1-methyl-1H-tetrazol-5-ylthiomethyl)-3-cephem-4-carboxylic acid, and 3,4-diacetoxybenzoyl chloride were treated to give Compound R.

(d) By the procedure described above, 3,4-diacetoxybenzoylchloride and 7β-[D(—)-α-(3-methyl-1-ureido)-α-phenylacetamido]-7α-methoxy-3-acetoxymethyl-3-cephem-4-carboxylic acid were treated to give Compound Z.

(e) By the procedure described above, 3,4-diacetoxybenzoyl chloride and 7β-[D(—)-α-(3-methyl-1-ureido)-α-phenylacetamido]-7α-methoxy-3-(1-methyl-1H-tetrazol-5-ylthiomethyl)-3-cephem-4-carboxylic acid were treated to give Compound AA.

EXAMPLE 9

7-[D(—)-α-{3-(3,4-Diacetoxybenzoyl)-3-methyl-1-ureido}-α-(4-hydroxyphenyl)acetamido]-3-(1,2,3-triazol-5-ylthiomethyl)-3-cephem-4-carboxylic acid (Compound J) (1.2 g) obtained by Example 6 was dissolved in methanol (10 ml). To the solution was added dropwise methanolic ammonia (0.075 g/ml) (3 ml) while stirring at temperature of from —15° to —10° C. followed by stirring the mixture at the same temperature for 30 minutes. The reaction mixture was poured into cold, diluted hydrochloric acid (100 ml) and the precipitate was recovered by filtration and washed with water. The precipitate was dissolved in acetone (100 ml), and the solution was treated with activated charcoal and evaporated at room temperature under reduced pressure to dryness. The residue was treated with diethyl ether (50 ml) to give 0.8 g of Compound I.

(a) By the procedure described above, Compound E was prepared from 7-[D(—)-α-{3-(3,4-diacetoxybenzoyl)-3-methyl-1-ureido}-α-phenylacetamido]-3-(1-methyl-1H-tetrazol-5-ylthiomethyl)-3-cephem-4-carboxylic acid (Compound R).

(b) By the procedure described above, Compound F was prepared from 7-[D(—)-α-{3-(3,4-diacetoxybenzoyl)-3-methyl-1-ureido}-α-(4-hydroxyphenyl)acetamido]-3-(1-methyl-1H-tetrazol-5-ylthiomethyl)-3-cephem-4-carboxylic acid (Compound S).

(c) By the procedure described above, Compound C was prepared from 7-[D(—)-α-{3-(3,4-diacetoxybenzoyl)-3-methyl-1-ureido}-α-phenylacetamido]-3-(5-methyl-1,3,4-thiadiazol-2-ylthiomethyl)-3-cephem-4-carboxylic acid (Compound P).

(d) By the procedure described above, Compound D was prepared from 7-[D(—)-α-{3-(3,4-diacetoxybenzoyl)-3-methyl-1-ureido}-α-(4-hydroxyphenyl)acetamido]-3-(5-methyl-1,3,4-thiadiazol-2-ylthiomethyl)-3-cephem-4-carboxylic acid (Compound Q).

(e) By the procedure described above, Compound G was prepared from 7-[D(—)-α-{3-(3,4-diacetoxybenzoyl)-3-methyl-1-ureido}-α-phenylacetamido]-3-(1,3,4-thiadiazol-2-ylthiomethyl)-3-cephem-4-carboxyxylic acid.

(f) By the procedure described above, Compound H was prepared from 7-[D(—)-α-{3-(3,4-diacetoxybenzoyl)-3-methyl-1-ureido}-α-(4-hydroxyphenyl)acetamido]-3-(1,3,4-thiadiazol-2-ylthiomethyl)-3-cephem-4-carboxylic acid.

(g) By the procedure described above, Compound K was prepared from 7-[D(—)-α-{3-(2,3-diacetoxybenzoyl)-1-ureido}-α-phenylacetamido]-3-(1-methyl-1H- tetrazol-5-ylthiomethyl)-3-cephem-4-carboxylic acid (Compound M).

(h) By the procedure described above, Compound L was prepared from 7-[D(−)-α-{3-(3,4-diacetoxybenzoyl)-1-ureido}-α-phenylacetamido]-3-(5-methyl-1,3,4-thiadiazol-2-ylthiomethyl)-3-cephem-4-carboxylic acid.

EXAMPLE 10

2-Diethylaminoethanol (1 ml) was added dropwise to a solution of Compound AA (350 mg) obtained by Example 5-(a) in dimethylformamide (1 ml) while cooling with ice-water. After stirring the mixture at room temperature for 5 hours, the mixture was poured into a mixture of ethyl acetate (50 ml), acetone (10 ml) and 2 N hydrochloric acid (50 ml) while stirring under cooling with ice-water. The organic layer was recovered, washed with a cold, saturated sodium chloride aqueous solution, dried over anhydrous magnesium sulfate and distilled under reduced pressure to remove the solvent used. The residue was treated with diethyl ether to give 230 mg of Compound T as a pale yellow powder.

(a) By the procedure described in this Example above, Compound A was prepared from Compound N obtained by Example 3-(2).

(b) By the procedure described above, Compound B was prepared from Compound O obtained by Example 3-(a).

(c) By the procedure described above, Compound U was prepared from 7β-[D(−)-α-{3-(3,4-diacetoxybenzoyl)-3-methyl-1-ureido}-α-phenylacetamido]-7α-methoxy-3-(5-methyl-1,3,4-thiadiazol-2-ylthiomethyl)-3-cephem-4-carboxylic acid.

(d) By the procedure described above, Compound V was prepared from 7β-[D(−)-α-{3-(3,4-diacetoxybenzoyl)-3-methyl-1-ureido}-α-phenylacetamido]-7α-methoxy-3-(1,3,4-thiadiazol-2-ylthiomethyl)-3-cephem-4-carboxylic acid.

EXAMPLE 11

7-[D(−)-α-{3-(3,4-Dihydroxybenzoyl)-3-methyl-1-ureido}-α-phenylacetamido]-3-acetoxymethyl-3-cephem-4-carboxylic acid (Compound A) (0.57 g) obtained by Example 1-(5) was suspended in a phosphoric acid buffer solution having a pH of 6.3 (10 ml). To the suspension was dissolved sodium bicarbonate (0.70 g) and then 5-methyl-2-mercapto-1,3,4-thiadiazole (0.13 g). The solution was subjected to reaction for 24 hours while keeping its pH in the range of from 6.0 to 6.5 with diluted hydrochloric acid and sodium bicarbonate and its temperature to 45°–55° C. The reaction mixture was cooled and washed with ethyl acetate and then the aqueous layer was recovered. The pH of the aqueous layer was adjusted to about 1.0 with diluted hydrochloric acid and the precipitate was recovered by filtration. The precipitate was washed with water (50 ml) and dissolved in acetone (20 ml). The solution was treated with activated charcoal and distilled at room temperature under reduced pressure to dryness. The residue was treated with diethyl ether (10 ml) to give Compound C as a pale yellow amorphous solid.

(a) By the procedure described above, Compound D was prepared from Compound B.

(b) By the procedure described above, Compound E was prepared from Compound A.

(c) By the procedure described above, Compound F was prepared from Compound B.

(d) By the procedure described above, Compound G was prepared from Compound A.

(e) By the procedure described above, Compound H was prepared from Compound B.

(f) By the procedure described above, Compound I was prepared from Compound B.

(g) By the procedure described above, Compound K was prepared from 7-[D(−)-α-{3-(2,3-dihydroxybenzoyl)-1-ureido}-α-phenylacetamido]-3-acetoxymethyl-3-cephem-4-carboxylic acid and 1-methyl-5-mercapto-1H-tetrazole.

(h) By the procedure described above, Compound L was prepared from 7-[D(−)-α-{3-(3,4-dihydroxybenzoyl)-1-ureido}-α-phenylacetamido]-3-acetoxymethyl-3-cephem-4-carboxylic acid and 5-methyl-2-mercapto-1,3,4-thiadiazole.

(i) By the procedure described above, Compound T was prepared from 7β-[D(−)-α-{3-(3,4-dihydroxybenzoyl)-3-methyl-1-ureido}-α-phenylacetamido]-7α-methoxy-3-acetoxymethyl-3-cephem-4-carboxylic acid (referred to as Compound AB hereunder) and 1-methyl-5-mercapto-1H-tetrazole.

(j) By the procedure described above, Compound U was prepared from Compound AB and 5-methyl-2-mercapto-1,3,4-thiadiazole.

(k) By the procedure described above, Compound V was prepared from compound AB+2-mercapto-1,3,4-thiadiazole.

Minimum inhibitory concentration (MIC) for several kinds of bacterial was determined with respect to the compounds of this invention prepared by Examples 1–11 and the results are shown in the following Table. In the Table, the bacteria used are referred to in terms of the following numbers.

| | |
|---|---|
| 1. *Bacillus subtilis* PCI-219 | 11. *Pseudomonas aeruginosa* J-272 |
| 2. *Staphylococcus aureus* 209 P | 12. *Pseudomonas aeruginosa* J-169 |
| 3. *Staphylococcus aureus* JU-5 | 13. *Pseudomonas aeruginosa* J-169-CM222 |
| 4. *Sarcina lutea* B | 14. *Pseudomonas aeruginosa* GNB-75 |
| 5. *Escherichia coli* NIHJ | 15. *Pseudomonas aeruginosa* GNB-75-M57740 |
| 6. *Shigella flexneri* 2b | 16. *Pseudomonas aeruginosa* KAN-2 |
| 7. *Salmonella paratyphi* A | 17. *Pseudomonas aeruginosa* Ps-6 |
| 8. *Klebsiella pneumoniae* 15C | 18. *Serratia marcescens* Ser-25b |
| 9. *Proteus mirabilis* 1287 | 19. *Serratia marcescens* FU-104 |
| 10. *Proteus morgani* JU-244 | 20. *Enterobacter clocae* FU-250 |

| Test Compound Bacteria | A | B | C | D | E | F | G | H | I | J | K | L | M | N | O | P | Q | R | S | T | Z | AA | cephaloridine | cefazorin |
|---|---|---|---|---|---|---|---|---|---|---|---|---|---|---|---|---|---|---|---|---|---|---|---|---|
| 1 | 0.4 | 0.4 | 0.4 | 0.78 | 0.4 | 0.78 | 0.4 | 0.78 | 0.78 | 0.78 | 3.12 | 1.56 | 3.12 | 0.4 | 0.2 | 0.78 | 0.2 | 0.78 | 0.4 | 3.12 | 6.25 | 3.12 | ≦0.025 | 0.20 |
| 2 | 0.78 | 0.78 | 0.4 | 0.78 | 0.4 | 0.78 | 0.2 | 0.4 | 0.78 | 0.4 | 1.56 | 0.78 | 0.78 | 0.78 | 1.56 | 0.78 | 0.78 | 1.56 | 1.56 | 1.56 | 6.25 | 1.56 | ≦0.013 | 0.10 |
| 3 | 3.12 | 6.25 | 3.12 | 3.12 | 3.13 | 3.13 | 1.56 | 3.12 | 3.12 | 3.12 | 6.25 | 3.12 | 6.25 | 3.12 | 6.25 | 1.56 | 3.12 | 3.12 | 6.25 | 1.56 | 6.25 | 3.12 | 0.2 | 0.78 |
| 4 | 0.78 | 0.78 | 0.4 | 0.4 | 0.2 | 0.2 | 0.2 | 0.4 | 0.4 | 0.2 | 0.78 | 0.4 | 0.4 | 0.4 | 0.4 | 0.78 | 0.2 | 0.78 | 0.2 | 0.4 | 1.56 | 3.12 | 0.025 | 0.40 |
| 5 | ≦0.1 | ≦0.1 | ≦0.1 | ≦0.1 | 0.1 | ≦0.1 | ≦0.1 | 0.39 | ≦0.1 | ≦0.1 | 0.78 | 0.78 | 0.78 | 0.1 | ≦0.05 | 0.2 | ≦0.05 | 0.2 | >0.05 | ≦0.05 | 0.1 | 0.1 | 6.25 | 1.56 |
| 6 | ≦0.1 | ≦0.1 | ≦0.1 | ≦0.1 | ≦0.2 | ≦0.1 | ≦0.1 | ≦0.1 | ≦0.1 | ≦0.1 | ≦0.1 | 1.56 | 1.56 | 0.1 | ≦0.05 | 0.2 | ≦0.05 | 0.2 | ≦0.05 | ≦0.05 | 0.2 | ≦0.05 | 6.25 | 1.56 |
| 7 | ≦0.1 | ≦0.1 | ≦0.1 | ≦0.1 | ≦0.1 | ≦0.1 | ≦0.1 | ≦0.1 | ≦0.1 | ≦0.1 | ≦0.1 | 0.78 | 1.56 | 0.2 | ≦0.05 | 0.2 | ≦0.05 | 0.4 | 0.1 | ≦0.05 | 0.2 | 0.1 | 3.13 | 1.56 |
| 8 | 0.2 | 0.2 | ≦0.1 | 0.4 | 0.1 | 0.1 | ≦0.1 | 0.2 | ≦0.1 | 0.4 | 1.56 | 1.56 | 1.56 | 0.2 | 0.1 | 0.2 | 0.1 | 0.4 | 0.1 | 0.1 | 0.4 | 0.2 | 3.13 | 1.56 |
| 9 | 0.78 | 0.78 | 0.4 | 0.78 | 0.4 | 0.78 | 0.4 | 0.78 | 0.4 | 0.4 | 6.25 | 6.25 | 6.25 | 1.56 | 1.56 | 3.12 | 0.78 | 3.12 | 1.56 | 1.56 | 3.12 | 1.56 | 6.25 | 3.12 |
| 10 | 1.56 | 1.56 | 0.4 | 0.78 | 0.4 | 0.4 | 0.4 | 0.4 | 0.2 | 3.12 | 6.25 | 25 | 12.5 | 0.78 | 1.56 | 1.56 | 0.39 | 1.56 | 0.78 | 0.39 | 1.56 | 0.78 | 400 | 100 |
| 11 | 0.4 | 0.2 | 0.4 | 0.4 | 0.4 | 0.78 | 0.4 | 0.4 | 3.12 | 0.4 | 12.5 | 25 | 12.5 | 0.4 | 0.2 | 1.56 | 0.2 | 1.56 | 0.4 | 0.4 | 3.12 | 0.4 | >400 | >400 |
| 12 | 0.4 | 1.56 | 0.4 | 0.78 | 0.78 | 0.78 | 0.78 | 1.56 | 3.12 | 3.12 | 6.25 | 1.56 | 0.2 | 3.12 | 0.4 | 3.12 | 0.4 | 3.12 | 0.78 | 0.78 | 1.56 | 0.78 | >400 | >400 |
| 13 | 3.12 | 1.56 | 1.56 | 6.25 | 1.56 | 3.12 | 6.25 | 6.25 | 25 | 25 | 6.25 | 6.25 | 0.1 | 6.25 | 3.12 | 6.25 | 1.56 | 6.25 | 1.56 | 0.78 | 6.25 | 1.56 | >400 | >400 |
| 14 | 3.12 | 3.12 | 3.12 | 1.56 | 3.12 | 3.12 | 6.25 | 6.25 | 50 | 50 | 12.5 | 6.25 | 12.5 | 0.2 | ≦0.05 | 6.25 | ≦0.05 | 6.25 | 0.2 | 0.1 | 6.25 | 0.1 | 800 | >400 |
| 15 | ≦0.1 | 0.2 | 0.2 | 0.78 | 0.39 | 0.78 | 0.4 | 0.4 | 0.78 | 1.56 | 0.2 | 0.1 | ≦12.5 | 12.5 | 0.4 | 0.4 | 0.2 | 0.78 | 0.2 | ≦0.05 | 0.4 | 0.1 | 1.56 | 3.12 |
| 16 | 0.4 | 0.4 | 0.4 | 0.4 | 0.4 | 0.4 | ≦0.1 | 0.2 | ≦0.1 | 0.1 | 0.2 | 1.56 | 0.2 | 0.4 | 0.4 | 0.2 | ≦0.05 | 0.4 | 0.4 | 0.4 | 0.4 | 0.4 | >400 | >400 |
| 17 | 0.78 | 0.78 | 0.78 | 0.78 | 0.78 | 0.78 | 0.78 | 0.78 | 1.56 | 1.56 | 0.78 | 6.25 | 0.78 | 1.56 | 0.78 | 3.13 | 0.78 | 3.13 | 1.56 | 0.78 | 1.56 | 1.56 | >400 | >400 |
| 18 | 0.78 | 0.4 | 0.4 | 1.56 | 0.4 | 1.56 | 0.78 | 0.78 | 6.25 | 6.25 | 6.25 | 50 | 6.25 | 1.56 | 1.56 | 1.56 | 0.39 | 1.56 | 0.78 | 0.20 | 1.56 | 0.39 | 50 | 400 |
| 19 | 1.56 | 6.25 | 0.78 | 1.56 | 0.78 | 1.56 | 0.4 | 1.56 | 0.78 | 0.78 | 100 | 200 | 100 | 1.56 | 1.56 | 1.56 | 0.78 | 3.13 | 0.78 | 0.39 | 3.13 | 0.78 | >400 | >400 |
| 20 | 0.4 | 0.78 | 0.4 | 1.56 | 0.78 | 1.56 | 0.78 | 3.13 | 0.4 | 0.4 | 6.25 | 50 | 6.25 | 0.39 | 0.39 | 0.78 | 0.39 | 0.39 | 0.20 | 0.20 | 0.78 | 0.20 | >400 | 400 |

What we claim is:

1. A cephalosporin derivative represented by the formula

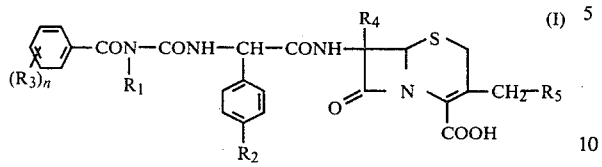

wherein $R_1$ is a hydrogen atom or a lower alkyl group; $R_2$ is a hydrogen atom or a hydroxyl group; $R_3$ is a hydroxyl group or a lower alkanoyloxyl group; n is 2 or 3; at least two of $R_3$ are bonded to adjacent carbon atoms, the position of substituent $R_3$ being selected from 3 to 5 position when $R_1$ is a lower alkyl group and $R_3$ is a hydroxyl group, and 2 to 6 position when $R_1$ and $R_3$ are other substituents; $R_4$ is a hydrogen atom; and $R_5$ is $-S-R_6$ (wherein $R_6$ is a five-membered heterocyclic ring selected from the group consisting of 1,3,4-thiadiazole, triazole and tetrazole, each of which is unsubstituted or substituted with a lower alkyl group) or a pharmaceutically acceptable salt thereof.

2. A cephalosporin derivative or a salt thereof according to claim 1 wherein $R_3$ is a hydroxyl group.

3. A cephalosporin derivative or a salt thereof according to claim 1 wherein $R_3$ is a hydroxyl group, and $R_5$ is,

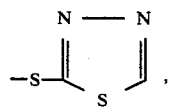

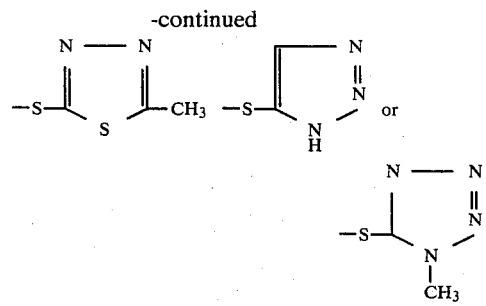

4. A cephalosporin derivative or a salt thereof according to claim 1 wherein the derivative is represented by the formula

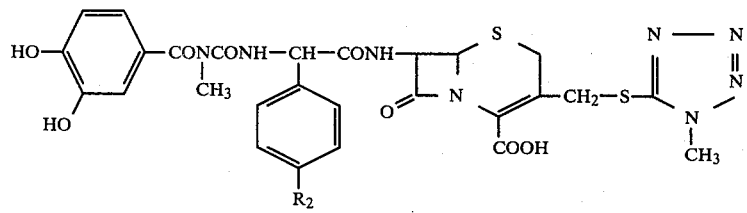

(wherein $R_2$ is a hydrogen atom or a hydroxyl group).

5. A cephalosporin derivative or a salt thereof according to claim 1 wherein $R_3$ is a lower alkanoyloxyl group.

6. A cephalosporin derivative or a salt thereof according to claim 5 wherein said lower alkanoyloxy group is an acetyloxyl group.

7. A cephalosporin derivative or a salt thereof according to claim 1 wherein $R_3$ is an acetyloxyl group and $R_5$ is

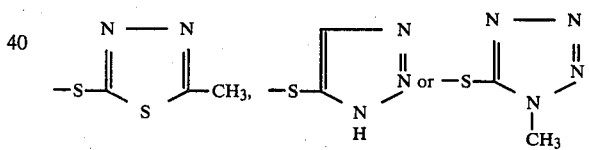

8. A cephalosporin derivative or a salt thereof according to claim 1 wherein said derivative is represented by the formula

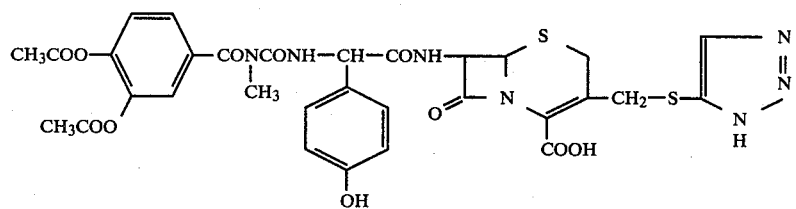

9. An antibacterial preparation comprising a pharmaceutical carrier and as active ingredient an antibacterial effective amount of a compound of any one of claims 1 or 2–8.

* * * * *

UNITED STATES PATENT AND TRADEMARK OFFICE
CERTIFICATE OF CORRECTION

PATENT NO. : 4,298,605
DATED : Nov. 3, 1981
INVENTOR(S) : Oi et al

It is certified that error appears in the above-identified patent and that said Letters Patent are hereby corrected as shown below:

IN THE TABLE: at column 27, the row corresponding to bacteria 5, row S, the sign before the no. 0.05 should be -- $\leqq$ --.

In the row corresponding to bacteria 6, column E, the no. should be --0.1--.

In the row corresponding to bacteria 15, column M, there should be no sign before the numerial "12.5."

Signed and Sealed this

Fifteenth Day of March 1983

[SEAL]

Attest:

GERALD J. MOSSINGHOFF

Attesting Officer

Commissioner of Patents and Trademarks